(12) United States Patent
Arizti et al.

(10) Patent No.: US 10,285,871 B2
(45) Date of Patent: *May 14, 2019

(54) ABSORBENT ARTICLE WITH SENSOR

(71) Applicant: The Procter & Gamble Company, Cincinnati, OH (US)

(72) Inventors: Blanca Arizti, Schmitten (DE); Erik John Hasenoehrl, Loveland, OH (US); Jonathan Livingston Joyce, Independence, KY (US); Mattias Schmidt, Idstein (DE); Faiz Feisal Sherman, Mason, OH (US); Steven Jeffrey Specht, Brookfeld, CT (US); Grant Edward Anders Striemer, Fairfield Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 473 days.

This patent is subject to a terminal disclaimer.

(21) Appl. No.: 15/134,035

(22) Filed: Apr. 20, 2016

(65) Prior Publication Data
US 2017/0252225 A1    Sep. 7, 2017

(30) Foreign Application Priority Data
Mar. 3, 2016   (EP) .................................... 16158532

(51) Int. Cl.
*A61F 13/15*  (2006.01)
*A61F 13/20*  (2006.01)
(Continued)

(52) U.S. Cl.
CPC .............. *A61F 13/42* (2013.01); *A61F 13/49* (2013.01); *A61F 13/58* (2013.01); *A61F 13/62* (2013.01);
(Continued)

(58) Field of Classification Search
CPC ................ A61F 13/42; A61F 2013/422; A61F 2013/423; A61F 2013/426; A61F 2013/427; A61F 2013/429
See application file for complete search history.

(56) References Cited

U.S. PATENT DOCUMENTS 3,848,594 A    11/1974 Buell
3,860,003 A    1/1975 Buell
(Continued)

FOREIGN PATENT DOCUMENTS

EP    0 149 880 A2    5/1984
EP    1 216 673 B1    10/2005
(Continued)

OTHER PUBLICATIONS

PCT International Search Report, dated May 4, 2017 (12 pages).

*Primary Examiner* — Michele M Kidwell
(74) *Attorney, Agent, or Firm* — Andrew J. Hagerty; Kelly L. McDow

(57) ABSTRACT

The present disclosure provides an absorbent article for personal hygiene. More particularly, in one embodiment, the absorbent article absorbent article includes at least one property changing indicator. A detector device is also provided that includes at least one sensor. The sensor is adapted to detect the property change of the property change indicator in the absorbent article. In one particular embodiment, for example, the property changing indicator may include an optical property indicator such as a color change indicator and the sensor may include an optical sensor such as a color sensor.

16 Claims, 12 Drawing Sheets

(51) Int. Cl.
  *A61F 13/42*    (2006.01)
  *A61F 13/58*    (2006.01)
  *A61F 13/62*    (2006.01)
  *A61F 13/64*    (2006.01)
  *G08B 21/20*    (2006.01)
  *A61F 13/49*    (2006.01)

(52) U.S. Cl.
  CPC .............. *A61F 13/64* (2013.01); *G08B 21/20*
          (2013.01); *A61F 2013/422* (2013.01); *A61F*
                *2013/423* (2013.01); *A61F 2013/424*
          (2013.01); *A61F 2013/426* (2013.01); *A61F*
                *2013/427* (2013.01); *A61F 2013/428*
                (2013.01); *A61F 2013/429* (2013.01)

(56) References Cited

U.S. PATENT DOCUMENTS

| | | | |
|---|---|---|---|
| 3,911,173 A | 10/1975 | Sprague, Jr. |
| 4,286,331 A | 8/1981 | Anderson |
| 4,515,595 A | 5/1985 | Kievit et al. |
| 4,554,662 A | 11/1985 | Suzuki |
| 4,573,986 A | 3/1986 | Minetola et al. |
| 4,662,875 A | 5/1987 | Hirotsu et al. |
| 4,681,793 A | 7/1987 | Linman et al. |
| 4,695,278 A | 9/1987 | Lawson |
| 4,699,622 A | 10/1987 | Toussant et al. |
| 4,710,189 A | 12/1987 | Lash |
| 4,785,996 A | 11/1988 | Ziecker et al. |
| 4,795,454 A | 1/1989 | Dragoo |
| 4,808,178 A | 2/1989 | Aziz et al. |
| 4,842,666 A | 6/1989 | Werenicz |
| 4,846,815 A | 7/1989 | Scripps |
| 4,894,060 A | 1/1990 | Nestegard |
| 4,909,803 A | 3/1990 | Aziz et al. |
| 4,940,464 A | 7/1990 | Van Gompel et al. |
| 4,946,527 A | 8/1990 | Battrell |
| 4,963,140 A | 10/1990 | Robertson et al. |
| 5,137,537 A | 8/1992 | Herron et al. |
| 5,151,092 A | 9/1992 | Buell et al. |
| 5,221,274 A | 6/1993 | Buell et al. |
| 5,242,436 A | 9/1993 | Weil et al. |
| 5,264,830 A | 11/1993 | Kline et al. |
| 5,354,289 A | 10/1994 | Mitchell et al. |
| 5,433,715 A | 7/1995 | Tanzer et al. |
| 5,469,145 A | 11/1995 | Johnson |
| 5,499,978 A | 3/1996 | Buell et al. |
| 5,507,736 A | 4/1996 | Clear et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,591,152 A | 1/1997 | Buell et al. |
| 5,607,414 A | 3/1997 | Richards et al. |
| 5,700,254 A | 12/1997 | McDowall et al. |
| 5,709,222 A | 1/1998 | Davallou |
| 5,714,156 A | 2/1998 | Schmidt et al. |
| 5,838,240 A | 11/1998 | Johnson |
| 5,865,823 A | 2/1999 | Curro |
| 5,902,222 A | 5/1999 | Wessman |
| 5,938,648 A | 8/1999 | LaVon et al. |
| 5,959,535 A | 9/1999 | Remsburg |
| 6,004,306 A | 12/1999 | Robles et al. |
| 6,160,198 A | 3/2000 | Roe et al. |
| 6,093,869 A | 7/2000 | Roe et al. |
| 6,121,509 A | 9/2000 | Ashraf et al. |
| 6,203,496 B1 | 3/2001 | Gael et al. |
| 6,372,951 B1 | 4/2002 | Ovanesyan et al. |
| 6,384,296 B1 | 5/2002 | Roe et al. |
| 6,432,098 B1 | 8/2002 | Kline et al. |
| 6,501,002 B1 | 12/2002 | Roe et al. |
| 6,534,149 B1 | 3/2003 | Daley et al. |
| 6,583,722 B2 * | 6/2003 | Jeutter .................. A61F 13/42 |
| | | | 340/572.2 |
| 6,603,403 B2 | 8/2003 | Jeutter et al. |
| 6,617,488 B1 | 9/2003 | Springer et al. |
| 6,632,504 B1 | 10/2003 | Gillespie et al. |
| 6,645,190 B1 | 11/2003 | Olson et al. |
| 6,645,569 B2 | 11/2003 | Cramer et al. |
| 6,863,933 B2 | 3/2005 | Cramer et al. |
| 6,946,585 B2 | 9/2005 | London Brown |
| 7,002,054 B2 | 2/2006 | Allen et al. |
| 7,049,969 B2 | 5/2006 | Tamai |
| 7,112,621 B2 | 9/2006 | Rohrbaugh et al. |
| 7,174,774 B2 | 2/2007 | Pawar |
| 7,241,627 B2 | 7/2007 | Wilhelm et al. |
| 7,250,547 B1 | 7/2007 | Hofmeister et al. |
| 7,295,125 B2 | 11/2007 | Gabriel |
| 7,355,090 B2 | 4/2008 | Ales, III et al. |
| 7,394,391 B2 | 7/2008 | Long |
| 7,449,614 B2 | 11/2008 | Alex, III |
| 7,477,156 B2 | 1/2009 | Long et al. |
| 7,489,252 B2 | 2/2009 | Long et al. |
| 7,498,478 B2 | 3/2009 | Long et al. |
| 7,504,550 B2 | 3/2009 | Tippey et al. |
| 7,524,195 B2 | 4/2009 | Ales et al. |
| 7,537,832 B2 | 5/2009 | Carlucci et al. |
| 7,595,734 B2 | 9/2009 | Long et al. |
| 7,642,396 B2 | 1/2010 | Alex, III et al. |
| 7,649,125 B2 | 1/2010 | Ales, III et al. |
| 7,659,815 B2 | 2/2010 | Cohen et al. |
| 7,667,806 B2 | 2/2010 | Ales et al. |
| 7,700,820 B2 | 4/2010 | Tippey et al. |
| 7,700,821 B2 | 4/2010 | Ales, III et al. |
| 7,737,322 B2 | 6/2010 | Alex, III et al. |
| 7,753,691 B2 | 7/2010 | Ales et al. |
| 7,760,101 B2 | 7/2010 | Ales, III et al. |
| 7,786,341 B2 | 8/2010 | Schneider et al. |
| 7,789,869 B2 | 9/2010 | Berland et al. |
| 7,803,319 B2 | 9/2010 | Yang et al. |
| 7,812,731 B2 | 10/2010 | Bunza et al. |
| 7,834,235 B2 | 11/2010 | Long et al. |
| 7,835,925 B2 | 11/2010 | Roe et al. |
| 7,846,383 B2 | 12/2010 | Song |
| 7,850,470 B2 | 12/2010 | Ales et al. |
| 7,855,653 B2 | 12/2010 | Rondoni et al. |
| 7,879,392 B2 | 2/2011 | Wenzel et al. |
| 7,946,869 B2 | 5/2011 | Ales et al. |
| 7,956,754 B2 | 6/2011 | Long |
| 7,973,210 B2 | 7/2011 | Long et al. |
| 7,977,529 B2 | 7/2011 | Berman et al. |
| 8,044,258 B2 | 10/2011 | Hietpas |
| 8,053,624 B2 | 11/2011 | Nhan et al. |
| 8,053,625 B2 | 11/2011 | Nhan et al. |
| 8,057,454 B2 | 11/2011 | Long et al. |
| 8,058,194 B2 | 11/2011 | Nhan et al. |
| 8,101,813 B2 | 1/2012 | Ales et al. |
| 8,111,165 B2 | 2/2012 | Ortega et al. |
| 8,115,643 B2 | 2/2012 | Wada et al. |
| 8,172,982 B2 | 5/2012 | Ales et al. |
| 8,173,380 B2 | 5/2012 | Yang et al. |
| 8,183,876 B2 | 5/2012 | Wada et al. |
| 8,196,270 B2 | 6/2012 | Mandzsu |
| 8,196,809 B2 | 6/2012 | Thorstensson |
| 8,207,394 B2 | 6/2012 | Feldkamp et al. |
| 8,215,973 B2 | 7/2012 | Ales et al. |
| 8,222,476 B2 | 7/2012 | Song et al. |
| 8,237,572 B2 | 8/2012 | Clement et al. |
| 8,248,249 B2 | 8/2012 | Clement et al. |
| 8,264,362 B2 | 9/2012 | Ales et al. |
| 8,274,393 B2 | 9/2012 | Ales et al. |
| 8,299,317 B2 | 10/2012 | Tippey et al. |
| 8,304,598 B2 | 11/2012 | Masbacher et al. |
| 8,314,284 B1 | 11/2012 | Novello |
| 8,334,226 B2 | 12/2012 | Nhan et al. |
| 8,334,425 B2 | 12/2012 | Ales et al. |
| 8,338,659 B2 | 12/2012 | Collins et al. |
| 8,350,694 B1 | 1/2013 | Trundle |
| 8,372,242 B2 | 2/2013 | Ales et al. |
| 8,372,766 B2 | 2/2013 | Nhan et al. |
| 8,378,167 B2 | 2/2013 | Allen et al. |
| 8,381,536 B2 | 2/2013 | Nhan et al. |
| 8,384,378 B2 | 2/2013 | Feldkamp et al. |
| 8,395,014 B2 | 3/2013 | Helmer et al. |

(56) References Cited

U.S. PATENT DOCUMENTS

| | | |
|---|---|---|
| 8,416,088 B2 | 4/2013 | Ortega et al. |
| 8,431,766 B1 | 4/2013 | Lonero |
| 8,440,877 B2 | 5/2013 | Collins et al. |
| 8,452,388 B2 | 5/2013 | Feldkamp et al. |
| 8,471,715 B2 | 6/2013 | Solazzo et al. |
| 8,507,746 B2 | 8/2013 | Ong et al. |
| 8,546,639 B2 | 10/2013 | Wada et al. |
| 8,563,801 B2 | 10/2013 | Berland et al. |
| 8,570,175 B2 | 10/2013 | Rahimi |
| 8,604,268 B2 | 12/2013 | Cohen et al. |
| 8,623,292 B2 | 1/2014 | Song et al. |
| 8,628,506 B2 | 1/2014 | Ales, III et al. |
| 8,882,731 B2 | 1/2014 | Suzuki et al. |
| 8,642,832 B2 | 2/2014 | Ales et al. |
| 8,697,933 B2 | 4/2014 | Ales, III et al. |
| 8,697,934 B2 | 4/2014 | Nhan et al. |
| 8,697,935 B2 | 4/2014 | Daanen |
| 8,698,641 B2 | 4/2014 | Abraham et al. |
| 8,742,198 B2 | 6/2014 | Wei et al. |
| 8,773,117 B2 | 7/2014 | Feldkamp et al. |
| 8,779,785 B2 | 7/2014 | Wada et al. |
| 8,785,716 B2 | 7/2014 | Schaefer et al. |
| 8,816,149 B2 | 8/2014 | Richardson et al. |
| 8,866,052 B2 | 10/2014 | Nhan et al. |
| 8,866,624 B2 | 10/2014 | Ales et al. |
| 8,884,769 B2 | 11/2014 | Novak |
| 8,889,944 B2 | 11/2014 | Abraham et al. |
| 8,920,731 B2 | 12/2014 | Nhan et al. |
| 8,933,291 B2 | 1/2015 | Wei et al. |
| 8,933,292 B2 | 1/2015 | Abraham et al. |
| 8,962,909 B2 | 2/2015 | Groosman et al. |
| 8,975,465 B2 | 3/2015 | Hong et al. |
| 8,978,452 B2 | 3/2015 | Johnson et al. |
| 8,988,231 B2 | 3/2015 | Chen |
| 9,018,435 B2 | 4/2015 | Kawashima |
| 9,034,593 B2 | 5/2015 | Martin et al. |
| 9,070,060 B2 | 6/2015 | Forster |
| 9,072,634 B2 | 7/2015 | Hundorf et al. |
| 9,168,185 B2 | 10/2015 | Berland et al. |
| 9,211,218 B2 | 12/2015 | Rinnert et al. |
| 9,295,593 B2 | 3/2016 | Van Malderen |
| 9,301,884 B2 | 4/2016 | Shah et al. |
| 9,314,381 B2 | 4/2016 | Curran et al. |
| 9,317,913 B2 | 4/2016 | Carney |
| 9,380,977 B2 | 7/2016 | Abir |
| 9,402,771 B2 | 8/2016 | Carney et al. |
| 9,585,795 B2 | 3/2017 | Boase et al. |
| 2002/0021220 A1 | 2/2002 | Dreyer |
| 2002/0070864 A1 | 6/2002 | Jeutter et al. |
| 2003/0105190 A1 | 6/2003 | Diehl et al. |
| 2003/0148684 A1 | 8/2003 | Cramer et al. |
| 2004/0064114 A1 | 4/2004 | David |
| 2004/0106202 A1 | 6/2004 | Zainiev et al. |
| 2004/0127867 A1 | 7/2004 | Odorzynski et al. |
| 2004/0236302 A1 | 11/2004 | Wilhelm et al. |
| 2004/0254549 A1 | 12/2004 | Olson et al. |
| 2005/0008839 A1 | 1/2005 | Cramer et al. |
| 2005/0065487 A1 | 3/2005 | Graef et al. |
| 2005/0099294 A1 | 5/2005 | Bogner |
| 2005/0124947 A1 | 6/2005 | Fernfors |
| 2005/0137542 A1 | 6/2005 | Underhill et al. |
| 2005/0195085 A1 | 9/2005 | Cretu-Petra |
| 2006/0222675 A1 | 10/2006 | Sabnis et al. |
| 2006/0264861 A1 | 11/2006 | Lavon |
| 2007/0055210 A1 | 3/2007 | Kao |
| 2007/0142797 A1 | 6/2007 | Long et al. |
| 2007/0156106 A1 | 7/2007 | Klofta |
| 2007/0185467 A1 | 8/2007 | Klofta et al. |
| 2007/0233027 A1 | 10/2007 | Roe et al. |
| 2007/0252710 A1 | 11/2007 | Long |
| 2007/0252711 A1 | 11/2007 | Long et al. |
| 2007/0252713 A1 | 11/2007 | Rondoni et al. |
| 2007/0255241 A1 | 11/2007 | Weber et al. |
| 2007/0255242 A1 | 11/2007 | Ales, III et al. |
| 2007/0282286 A1* | 12/2007 | Collins ............... A61F 13/42 604/361 |
| 2008/0021428 A1 | 1/2008 | Klofta et al. |
| 2008/0052030 A1 | 2/2008 | Olson et al. |
| 2008/0054408 A1 | 3/2008 | Tippey et al. |
| 2008/0057693 A1 | 3/2008 | Tippey et al. |
| 2008/0058740 A1 | 3/2008 | Sullivan et al. |
| 2008/0058741 A1 | 3/2008 | Long et al. |
| 2008/0074274 A1 | 3/2008 | Hu |
| 2008/0082063 A1 | 4/2008 | Ales |
| 2008/0132859 A1 | 6/2008 | Pires |
| 2008/0147031 A1 | 6/2008 | Long et al. |
| 2008/0208155 A1 | 8/2008 | Lavon |
| 2008/0234644 A1 | 9/2008 | Hansson et al. |
| 2008/0266117 A1 | 10/2008 | Song et al. |
| 2008/0266122 A1 | 10/2008 | Ales et al. |
| 2008/0266123 A1 | 10/2008 | Ales |
| 2008/0269707 A1 | 10/2008 | Song |
| 2008/0300559 A1 | 12/2008 | Gustafson et al. |
| 2008/0312622 A1 | 12/2008 | Hundorf et al. |
| 2009/0058072 A1 | 3/2009 | Weber et al. |
| 2009/0062756 A1 | 3/2009 | Long et al. |
| 2009/0124990 A1 | 5/2009 | Feldkamp et al. |
| 2009/0155753 A1 | 6/2009 | Ales et al. |
| 2009/0326409 A1 | 12/2009 | Cohen et al. |
| 2010/0013778 A1 | 1/2010 | Liu |
| 2010/0030173 A1 | 2/2010 | Song et al. |
| 2010/0145294 A1 | 6/2010 | Song et al. |
| 2010/0152688 A1 | 6/2010 | Handwerker et al. |
| 2010/0159599 A1 | 6/2010 | Song et al. |
| 2010/0159611 A1 | 6/2010 | Song et al. |
| 2010/0160882 A1 | 6/2010 | Lowe |
| 2010/0164733 A1* | 7/2010 | Ales ............... A61F 13/42 340/604 |
| 2010/0168694 A1 | 7/2010 | Gakhar et al. |
| 2010/0168702 A1 | 7/2010 | Ales et al. |
| 2010/0241094 A1 | 9/2010 | Sherron |
| 2011/0251038 A1 | 10/2011 | Lavon |
| 2011/0298597 A1 | 12/2011 | Kaihori |
| 2012/0061016 A1 | 3/2012 | Lavon |
| 2012/0116337 A1* | 5/2012 | Ales ............... A61F 13/42 604/361 |
| 2012/0130330 A1 | 5/2012 | Wilson et al. |
| 2012/0157947 A1 | 6/2012 | Nhan et al. |
| 2012/0161960 A1 | 6/2012 | Cheng |
| 2012/0172824 A1 | 7/2012 | Khaknazarov |
| 2012/0190956 A1 | 7/2012 | Connolly |
| 2012/0206265 A1 | 8/2012 | Solazzo |
| 2012/0225200 A1 | 9/2012 | Mandzsu |
| 2012/0245542 A1 | 9/2012 | Suzuki et al. |
| 2012/0282681 A1 | 11/2012 | Teixeira et al. |
| 2012/0299721 A1 | 11/2012 | Jones |
| 2012/0310190 A1 | 12/2012 | LaVon et al. |
| 2012/0310191 A1* | 12/2012 | LaVon ............... A61F 13/505 604/361 |
| 2012/0310192 A1 | 12/2012 | Suzuki et al. |
| 2012/0323194 A1 | 12/2012 | Suzuki et al. |
| 2013/0012896 A1 | 1/2013 | Suzuki et al. |
| 2013/0018340 A1 | 1/2013 | Abraham et al. |
| 2013/0023786 A1 | 1/2013 | Mani et al. |
| 2013/0041334 A1 | 2/2013 | Prioleau et al. |
| 2013/0076509 A1 | 3/2013 | Ahn |
| 2013/0110061 A1 | 5/2013 | Abraham et al. |
| 2013/0110063 A1 | 5/2013 | Abraham |
| 2013/0131618 A1 | 5/2013 | Abraham et al. |
| 2013/0151186 A1 | 6/2013 | Feldkamp |
| 2013/0161380 A1 | 6/2013 | Joyce et al. |
| 2013/0162402 A1 | 6/2013 | Amann et al. |
| 2013/0162403 A1 | 6/2013 | Stiemer et al. |
| 2013/0162404 A1 | 6/2013 | Stiemer et al. |
| 2013/0165809 A1 | 6/2013 | Abir |
| 2013/0261409 A1 | 10/2013 | Pathak |
| 2013/0303867 A1 | 11/2013 | Elfström et al. |
| 2013/0307570 A1 | 11/2013 | Bosaeus et al. |
| 2013/0321007 A1 | 12/2013 | Elfström et al. |
| 2013/0324955 A1 | 12/2013 | Wong et al. |
| 2014/0005622 A1 | 1/2014 | Wirtz et al. |
| 2014/0014716 A1 | 1/2014 | Joyce et al. |
| 2014/0015644 A1 | 1/2014 | Amann et al. |

(56) References Cited

U.S. PATENT DOCUMENTS

| | | |
|---|---|---|
| 2014/0015645 A1 | 1/2014 | Stiemer et al. |
| 2014/0022058 A1 | 1/2014 | Stiemer et al. |
| 2014/0062663 A1 | 3/2014 | Bourilkov et al. |
| 2014/0121487 A1 | 5/2014 | Faybishenko et al. |
| 2014/0152442 A1 | 6/2014 | Li |
| 2014/0155850 A1 | 6/2014 | Shah et al. |
| 2014/0155851 A1 | 6/2014 | Ales et al. |
| 2014/0163502 A1 | 6/2014 | Arzti et al. |
| 2014/0188063 A1 | 7/2014 | Nhan et al. |
| 2014/0200538 A1 | 7/2014 | Euliano et al. |
| 2014/0241954 A1 | 8/2014 | Phillips et al. |
| 2014/0242613 A1 | 8/2014 | Takeuchi et al. |
| 2014/0242715 A1 | 8/2014 | Nhan et al. |
| 2014/0244644 A1 | 8/2014 | Maschinchi et al. |
| 2014/0292520 A1 | 10/2014 | Carney et al. |
| 2014/0033442 A1 | 11/2014 | Carney |
| 2014/0329212 A1 | 11/2014 | Ruman et al. |
| 2014/0329213 A1 | 11/2014 | Ruman et al. |
| 2014/0363354 A1 | 12/2014 | Phillips et al. |
| 2014/0371702 A1 | 12/2014 | Bosae et al. |
| 2015/0025347 A1 | 1/2015 | Song |
| 2015/0042489 A1 | 2/2015 | LaVon |
| 2015/0112202 A1 | 4/2015 | Abir |
| 2015/0130637 A1 | 5/2015 | Sengstaken, Jr. |
| 2015/0143881 A1 | 5/2015 | Raut et al. |
| 2015/0150732 A1 | 6/2015 | Abir |
| 2015/0157512 A1 | 6/2015 | Abir |
| 2015/0206151 A1 | 7/2015 | Carney et al. |
| 2015/0209193 A1 | 7/2015 | Ying et al. |
| 2015/0223755 A1* | 8/2015 | Abir ............... A61F 13/42 600/300 |
| 2015/0317684 A1 | 11/2015 | Abir |
| 2016/0008182 A1 | 1/2016 | Prokopuk et al. |
| 2016/0051416 A1 | 2/2016 | Vartiainen et al. |
| 2016/0051417 A1 | 2/2016 | Chu |
| 2016/0067113 A1 | 3/2016 | Vartiainen et al. |
| 2016/0078716 A1 | 3/2016 | Olafsson-Ranta et al. |
| 2016/0080841 A1 | 3/2016 | Bergstrom et al. |
| 2016/0113822 A1 | 4/2016 | Vartiainen et al. |
| 2016/0134497 A1 | 5/2016 | Hermansson et al. |
| 2016/0170776 A1 | 6/2016 | Bergstrom et al. |
| 2016/0235603 A1 | 8/2016 | Ehrnsperger et al. |
| 2016/0374868 A1 | 12/2016 | Ettrup Hansen |
| 2017/0252225 A1 | 9/2017 | Arizti et al. |

FOREIGN PATENT DOCUMENTS

| | | |
|---|---|---|
| EP | 1 542 635 B1 | 4/2012 |
| EP | 2 491 899 B1 | 7/2014 |
| JP | 09-187431 | 7/1997 |
| JP | 2002/022687 A | 1/2002 |
| JP | 2002/143199 A | 5/2002 |
| JP | 2003/190209 A | 7/2003 |
| JP | 2004/230135 A | 8/2004 |
| JP | 2006/296566 A | 11/2006 |
| WO | WO 95/016746 | 6/1995 |
| WO | WO 99/034841 | 7/1999 |
| WO | WO 2010/123364 A1 | 10/2010 |
| WO | WO 2010/123425 A1 | 10/2010 |
| WO | WO 2011/013874 A1 | 2/2011 |
| WO | WO 2012/084925 A1 | 6/2012 |
| WO | WO 2012/126507 A1 | 9/2012 |
| WO | WO 2013/003905 A1 | 1/2013 |
| WO | WO 2013/016765 A1 | 2/2013 |
| WO | WO 2013/061963 A1 | 5/2013 |
| WO | WO 2013/091707 A1 | 6/2013 |
| WO | WO 2013/091728 A1 | 6/2013 |
| WO | WO 2013/095222 A1 | 6/2013 |
| WO | WO 2013/095226 A1 | 6/2013 |
| WO | WO 2013/095230 A1 | 6/2013 |
| WO | WO 2013/095231 A1 | 6/2013 |
| WO | WO 2013/097899 A1 | 7/2013 |
| WO | WO 2013/181436 A1 | 12/2013 |
| WO | WO 2013/185419 A1 | 12/2013 |
| WO | WO 2013/189284 A1 | 12/2013 |
| WO | WO 2014/035302 A1 | 3/2014 |
| WO | WO 2014/035340 A1 | 3/2014 |
| WO | WO 2014/122169 A1 | 8/2014 |
| WO | WO 2014/137671 A1 | 9/2014 |
| WO | WO 2014/146693 A1 | 9/2014 |
| WO | WO 2014/146694 A1 | 9/2014 |
| WO | WO 2014/148957 A1 | 9/2014 |
| WO | WO 2014/177200 A1 | 11/2014 |
| WO | WO 2014/177203 A1 | 11/2014 |
| WO | WO 2014/177204 A1 | 11/2014 |
| WO | WO 2014/177205 A1 | 11/2014 |
| WO | WO 2014/178763 A1 | 11/2014 |
| WO | WO 2014/192978 A1 | 12/2014 |
| WO | WO 2015/003712 A1 | 1/2015 |
| WO | WO 2015/068124 A1 | 5/2015 |
| WO | WO 2015/102084 A1 | 7/2015 |
| WO | WO 2015/102085 A1 | 7/2015 |

* cited by examiner

ABSORBENT ARTICLE WITH SENSOR

CROSS-REFERENCE TO RELATED APPLICATIONS

This application claims priority to European Application Serial No. 16158532.8, filed on Mar. 3, 2016. This European application is hereby incorporated by reference as though fully set forth herein.

FIELD OF THE INVENTION

The present disclosure is directed to an absorbent article for personal hygiene and a system for monitoring such an absorbent article.

BACKGROUND

Absorbent articles for personal hygiene are designed to absorb and contain bodily exudates, such as a large quantity of urine. Non-limiting examples of disposable absorbent articles include diapers, pants, training pants, pads, adult incontinence products, and feminine hygiene products (including, for example, sanitary napkins and tampons). Other examples of disposable absorbent articles include bandages and wound dressings. In some embodiments, for example, an absorbent article comprises several layers providing different functions, for example a topsheet, a backsheet and in-between an absorbent core, among other layers.

The function of the absorbent core is to absorb and retain the exudates for a prolonged amount of time, for example overnight for a diaper, minimize re-wet to keep the wearer dry and avoid soiling of clothes or bed sheets. The majority of currently marketed absorbent articles comprise as absorbent material a blend of comminuted wood pulp with superabsorbent polymers (SAP) in particulate form, also called absorbent gelling materials (AGM), see for example U.S. Pat. No. 5,151,092 (Buell). Absorbent articles having a core consisting essentially of SAP as absorbent material (so called "airfelt-free" cores) have also been proposed but are less common than traditional mixed cores (see e.g. WO2008/155699 (Hundorf), WO95/11652 (Tenzer), WO2012/052172 (Van Malderen)).

U.S. Pat. No. 8,111,165 B2 discloses a sensor to sense a condition such as pressure from body weight or moisture from incontinence. The sensor comprises a signal processing unit, a transmitter and a power supply, typically in form of a battery. These elements are arranged on a flexible substrate in low profile enabling disposition adjacent to the human body. Moreover, a transmitter antenna is to be provided on the substrate.

While this device allows monitoring conditions of the human body and can also be used as a moisture sensor, it represents also relatively costly solution. It would not be seen appropriate to dispose of the sensor together with a (disposable) absorbent article. If the sensor, however, is to be reused, the sensing area has potentially been exposed to moisture. Therefore this concept does not allow for simple usage.

SUMMARY

In one embodiment, a system for monitoring an absorbent article designed to absorb and contain one or more bodily exudates is provided. In this embodiment, the system includes an absorbent article and a detector device. The absorbent article comprises at least one property changing indicator. The property changing indicator is adapted to change at least one physical, chemical or biological property in response to the presence or absence of bodily exudates. The absorbent article and the indicator form one integral unit. The detector device comprises a first sensor adapted to detect the change of at least one physical, chemical or biological property of the at least one indicator at a first location of the absorbent article and a second sensor adapted to detect the change of at least one physical chemical or biological property of the at least one indicator at a second location of the absorbent article spaced from the first location. At least one of the absorbent article and the detector device is adapted to be associated together and disassociated from each other, wherein when the absorbent article and the detector device are associated together the detector device is adapted to detect the change of property of the indicator.

In another embodiment, a system for monitoring an absorbent article designed to absorb and contain bodily exudates is provided. In this embodiment, the system includes an absorbent article and a detector device. The absorbent article comprises an optical property changing indicator adapted to change at least one optical property in response to the presence or absence of bodily exudates. The absorbent article and the indicator form one integral unit. The optical sensor detector device comprises a housing, an optical sensor and a light spaced from the optical sensor. The optical sensor is adapted to detect the change of the optical property of the indicator. At least one of the absorbent article and the detector device is adapted to be associated together and disassociated from each other, wherein when the absorbent article and the detector device are associated together the detector device is adapted to detect the change of optical property of the indicator.

In yet another embodiment, an absorbent article is provided. The absorbent article comprises a back sheet, a top sheet and an absorbent core disposed between the back sheet and the top sheet. The absorbent article further comprises an optical property changing indicator disposed within the absorbent article. The optical property indicator is adapted to change an optical property of the optical property changing indicator in response to one or more bodily exudates within the absorbent article. The absorbent article also comprises a property changing indicator disposed in the absorbent article and spaced from the optical property indicator. The property changing indicator is adapted to change a physical, chemical or biological property of the property changing indicator in response to the presence or absence of one or more bodily exudates.

In still another embodiment, a detector device is provided. The detector device comprises a housing, a light, an optical sensor spaced from the light, a communication module and at least one battery adapted to provide power to the light and optical sensor. The optical sensor is adapted to detect a change in at least one of optical property of an absorbent article.

In another embodiment, an absorbent article is provided. The absorbent article comprises a back sheet, a top sheet and an absorbent core disposed between the back sheet and top sheet. The absorbent article further comprises an optical property changing indicator disposed within the absorbent article. The optical property changing indicator is adapted to change an optical property of the optical property changing indicator in response to one or more bodily exudates within the absorbent article. The absorbent article also comprises a property changing indicator disposed in the absorbent article and spaced from the optical property indicator. The property changing indicator is adapted to change a physical, chemical or biological property of the property changing indicator in response to the presence or absence of one or more bodily exudates.

In yet another embodiment, a method of monitoring an absorbent article is provided. The method comprises detecting an absence or presence of a bodily exudate in an absorbent article. The method also comprises altering at least one physical, chemical or biological property of an indicator in the diaper in response to a detection of the absence or presence of the bodily exudate in the absorbent article. The method further detects the change in the at least one physical, chemical or biological property of the indicator via a detector device comprising a spaced sensor and light pair.

DETAILED DESCRIPTION OF THE INVENTION

Introduction

Figure 1:
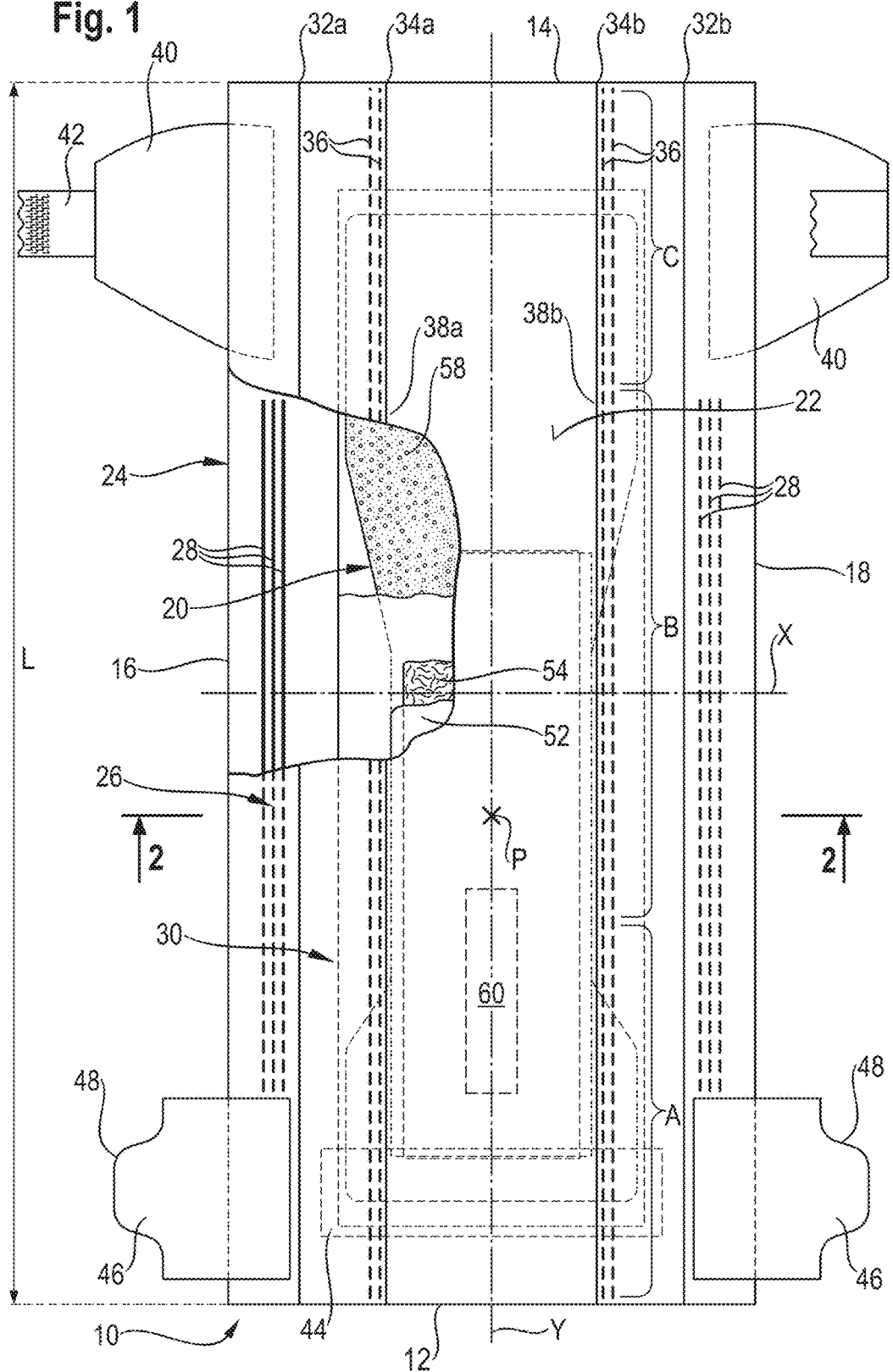
FIG. 1 is a top view of an absorbent article according to an embodiment of the present invention in the form of a diaper with some layers partially removed.

As used herein, the term "absorbent article" refers to disposable devices such as infant or adult diapers or pads, pants, training pants, and the like which are placed against or in proximity to the body of the wearer to absorb and contain the various exudates discharged from the body. Typically these articles comprise a topsheet, backsheet, an absorbent core and optionally an acquisition system (which may be comprised of one or several layers) and typically other components, with the absorbent core normally placed between the backsheet and the acquisition system or topsheet.

The absorbent articles of the invention will be further illustrated in the below description and in the Figures in the form of a taped diaper. Nothing in this description should be however considered limiting the scope of the claims unless explicitly indicated otherwise. Unless indicated otherwise, the description refers to the dry article, i.e. before use and conditioned at least 24 hours at 21° C.+/−2° C. and 50+/−20% Relative Humidity (RH).

A "nonwoven web" as used herein means a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding and airlaying. The basis weight of nonwoven webs is usually expressed in grams per square meter (g/m² or gsm).

The terms "joined" or "bonded" or "attached", as used herein, encompasses configurations whereby an element is directly secured to another element by affixing the element directly to the other element, and configurations whereby an element is indirectly secured to another element by affixing the element to intermediate member(s) which in turn are affixed to the other element. The terms further include embodiments in which a pocket or other connector is formed in or attached to an area of the absorbent article. Further, these terms include configurations in which the elements are removably, or non-removably, joined, bonded, or attached. For example, wherein an element is described as "joined" within the configuration, it may be either removably joined or non-removably joined unless otherwise specified or evident from the context.

The terms "comprise," "comprising," and "comprises" are open ended terms, each specifies the presence of what follows, e.g., a component, but does not preclude the presence of other features, e.g., elements, steps, components known in the art, or disclosed herein. These terms based on the verb "comprise" should be read as encompassing the narrower terms "consisting of" which excludes any element, step, or ingredient not specified and "consisting essentially of" which limits the scope of an element to the specified materials or steps and those that do not materially affect the way the element performs its function. Any preferred or exemplary embodiments described below are not limiting the scope of the claims, unless specifically indicated to do so. The words "typically", "normally", "advantageously" and the likes also qualify elements which are not intended to limit the scope of the claims unless specifically indicated to do so.

General Description of the Absorbent Article

The absorbent article comprises one or more indicator(s) adapted to indicate the presence and/or absence of bodily exudates. The indicator, in some embodiments, for example, may comprise an indicator that reacts to the presence and/or absence of bodily exudate(s) and/or one or more properties of those bodily exudates(s) within the absorbent article via one or more change in property of the indicator (e.g., a physical, chemical or biological property such as color, smell, sound, pH, or the like). One or more property or state of the indicator, in turn, may be detected by a detector device physically and/or communicatively coupled to the absorbent article. In one particular implementation, for example, the indicator comprises an optical property changing composition or device (e.g., a color-changing composition or device, such as a color changing indicator) that changes an optical property (e.g., color) in response to a variation of pH associated with the presence and/or absence of bodily exudates within the absorbent article). The indicator might also comprise one or more additional indicators of the same or different type that provide different types of indications and/or indications of bodily exudates (or properties of bodily exudates) detected in one or more different regions of the absorbent article. In one embodiment, for example, a second electrical indicator may comprise a resistance, capacitance, inductance or continuity sensitive indicator. A resistance sensitive indicator can be provided, for example, by providing two electrical conductors disposed at a given spatial distance relative to each other. If bodily exudates, which typically comprise a liquid portion, come in contact with the two electrical conductors, the resistance between the two electrical conductors is reduced. Other indicators, as known in the field in the context for sensor for absorbent articles, can also be useful. In one particular embodiment, for example, the multiple property changing indicators may be provided in the same or different locations within the absorbent article. For example, an optical property changing indicator (e.g., color changing indicator) may be disposed in a first location of an absorbent article and a second property changing indicator that is the same or a different type of indicator (e.g., another optical property changing indicator such as a color changing indicator) may be disposed in a second location of the absorbent article.

The absorbent article and the one or more indicators are provided to form an integral unit. For forming the integral unit, the indicator(s) can be directly or indirectly attached to the absorbent article. Direct or indirect attachment to the article is typically to one or more distinguishable element of the article. For example, it can be useful to attach the indicator(s) to the back sheet of the article, such that the indicator(s) and the back sheet of the article from one integral unit. For example if the indicator(s) are provided in sheet form, the respective sheet can be adhesively attached to the back sheet of the article. The respective sheet could also be provided from one and the same material with the back sheet, this material however being treated in suitable ways as to provide an indicator in a pre-defined area.

According to one particular embodiment, a detector device is also provided. The detector device, in this implementation, comprises a housing and is adapted to be physically coupled to the absorbent article such that the detector device is further communicatively coupled to one or more indicator integral with the absorbent article. The detector device and/or the absorbent article may comprise one or more connector for removably joining the detector device with the absorbent article. The connector(s) are provided such that the detector device can be attached to the absorbent article and can be detached from the absorbent article including the one or more indicator(s). The detector device can be attached to the integral unit and can be detached from the integral unit. In one particular embodiment, for example, the detector device can be attached to an area of the absorbent article juxtaposed the indicator integral to the absorbent article, and can be detached from that area of the absorbent article.

The housing of the detector device, in one embodiment, has an outer extension in a first direction and an outer extension in a second direction, which is perpendicular to the first direction. The first direction, in this embodiment, may be chosen as characteristic directions, e.g. along a main axis and normally as that of largest extension of the housing. For safety and convenient handling of the device, it may be useful that the device has a length in the first direction of at least 1 cm, 2 cm, 3 cm, 4 cm or more (but normally less than 15 cm) and that the device has a length in the second direction of at least 1 cm, 2 cm, 3 cm or more (but normally less than 15 cm). In one particular embodiment, for example, the housing has a first dimension of at least about one inch and a second dimension of at least about two inches. In various embodiments, the housing can be rigid or at least partially or fully flexible. To be flexible the detector device can incorporate flexible electronic components (and boards).

According to one embodiment, the detector device comprises one or more optical sensor, such as a color sensor. This optical sensor can generate an output which depends on an optical property (e.g., a color) observed by the optical sensor. Some examples of optical sensors across a range of wavelengths are: electron tube detectors, photosensors, photomultiplier tubes, phototubes, photodetectors, opto-semiconductor detectors, photodiodes, photomultipliers, image sensors, infrared detectors, thermal sensors, illuminance sensors, visible light sensors and color sensors. In one particular embodiment, for example, the optical sensor may comprise a photodiode such as a TCS 34725 color sensor commercially available from AMS-TAOS USA Inc.

In other embodiments, for example, the detector device need not include a light source, such as where sufficient ambient light may be provided in an application, where light is provided elsewhere (e.g., associated with an absorbent article or clothing, or elsewhere in an environment) or where the property change of a property changing indicator may be detectable without light.

Often, the detector device will also comprise one or more light, such as a light emitting diode (LED), organic light emitting diode (OLED), an incandescent light bulb, thermionic light emission, luminescence (e.g., among others, fluorescence, chemilluminescence, electroluminescence (e.g., LED), for emitting light onto an area, the wavelength or spectrum of which is to be assessed by the optical sensor. The optical sensor in some color detecting embodiments can be optimized for assessing a color of a color-changing indicator. The optical sensor can be sensitive to visible and non-visible light, namely light in the near IR range. In various embodiments, UV, visible infrared and near infrared wavelengths may be used. A color changing indicator can change its color, for example, based on the presence and/or absence of bodily exudates and/or in response to some other condition being monitored with respect to the absorbent article. In this embodiment, the color sensor can provide an output that varies depending on the presence or absence of bodily exudates.

In various embodiments, essentially any known color-changing indicator that responds to the absence or presence of bodily exudates or other conditions to be monitored with respect to the absorbent article can be useful. It may be useful to employ a color-changing indicator which comprises a chemical substance. Such a chemical substance can induce a color change when bodily exudates are present. One useful form of a color-changing indicator comprises a pH-sensitive indicator. Bodily exudates, for example, may influence the pH-value in their environment. Similarly, components within an absorbent article may alter a pH of the environment in response to contact with one or more bodily exudates. In one particular embodiment, for example, as AGM swells in the presence of urine or other liquids present in a bodily exudate, the AGM swelling changes the pH of the environment within the absorbent article. Thus, in this and other embodiments, a pH-sensitive indicator can be used and detected by the detector device.

Other useful indicators can comprise biological or physical sensor materials. The skilled person is aware of numerous useful biological sensor materials. Physical sensors can be provided by a material, which changes its color when the material is stretched. Stretching of a material can be induced by the swelling of the absorbent core. Biological sensors may include a bioreceptor that interacts with an analyte of interest, such as trypsin or urease. A bioreceptor, for example, may use reagent/analyte interactions that provide a property change (e.g., a color or other optical change) in the absorbent article upon detection of a particular analyte of interest. In one particular embodiment, for example, a bioreceptor may use an immobilised binding reagent also capable of binding to an analyte of interest. The immobilized reagent for example, may be disposed at a detection zone detectable by a sensor of a detector device.

Additionally the indicator can comprise a material selected from the group comprising, consisting essentially of or consisting of: thermochromic inks, thermochromic dyes, thermochromic liquid crystalline materials, and combinations thereof. These indicators can, for example, serve to monitor other conditions associated with the absorbent article and/or wearer of the absorbent article, such as body temperature or fever indication.

The present embodiments can usefully employ one or more connectors which allow for detachment and can also allow for refastening of an indication device to the absorbent article. Such connectors may comprise one or more adhesives or cohesives. Such connectors may further comprise one or more mechanical fasteners, including strap based fasteners or fasteners comprising at least one button or at least one magnet. Among the group of mechanical fasteners, a hook-end-loop fastener is useful. It can be useful to attach the hook-portion to the absorbent article or to attach the loop-portion to the absorbent article. The corresponding portion can then be attached to the detector device.

In one useful embodiment, the loop portion of a hook-and-loop-fastener can be provided integral with the absorbent article. For example, if the outer side of the backsheet of the absorbent article is provided from a textile material, e.g. a non-woven material, loops provided in such a material can interact with the hooks of a hook-portion of a fastener.

There are also alternative forms of mechanical fasteners (to be used as connectors), which can be used additionally or alternatively. For example, a pocket can be formed in an area of the absorbent article. For example, such a pocket can be formed between layers of the backsheet. A pocket can also be formed between other layers. For example, diapers can be provided as pant-diapers comprising a crotch-portion and a belt-portion. The crotch-portion and the belt-portion can be joined adhesively or mechanically, e.g. by crimping. In the area of adhesive joining, a certain portion can be free of adhesive and accessible from the outside. This portion can than serve as a pocket for receiving the detector device. A belt, strap or other device may be used to place and hold the detector device relative to the absorbent article. The detector device may similarly be joined or held to an article of clothing worn by the user wearing the absorbent article.

The detector device provides information which in one aspect will indicate the presence and/or absence of bodily exudates. Such a detector device can comprise a variety of output and/or display elements. A simple output element can comprise LED, OLED or similar lamps. For example a green light can be used as an indication for the absence of bodily exudates or presence only a low amount of bodily exudates whereas a red light can indicate the presence of a higher amount of bodily exudates and therefore will normally indicate the need to change the absorbent article. Information can be provided in more comprehensive forms and therefore a display element, for example in the form of a small monitor can be useful. Information to be displayed on such a monitor or similar display element could include information about the loading status of the absorbent article, the time at which a fresh absorbent article has been applied and so forth.

The output element or display element can be provided within the housing or attached to the detector device. The output element, for example, may include a visual output device (e.g., display, LED or the like), an audible output device (e.g., a speaker), a tactile output device and/or the like.

The output or display element can also be provided in a separate unit. Such a separate unit can also have other functions. It can be useful to employ a mobile phone with a display or another personal digital assistant for use as a display element in the present context. The display element can also be a computer (including a laptop computer or a tablet computer). Information obtained from the detector device can also be displayed on several such units at the same time. This can be displayed there in the same format or in similar formats. For example a more detailed display of information on a computer can be combined with simplified display of information on a mobile phone. Additionally or alternatively the output element can also comprise acoustic indication device and can also rely on a computer generated voice. In some cases also, the information is not or not only displayed or provided, but directed to a data storage device for data aggregation.

In one particular implementation, the separate unit may include any display or output device in the area surrounding the detector device (e.g., within a house, apartment or the like). The separate unit may further include a plurality of input/output nodes that may be communicatively coupled to the detector, such as an Amazon® Echo® device that may provide visual and/or audio outputs (e.g., "diaper needs changing").

For providing information to the separate unit the detector device can broadcast or otherwise send information to the unit comprising the display element. The skilled person is aware of useful standards for providing such broadcasting, for example Bluetooth, BTLE, mesh (e.g., IEEE 802.15.4), WiFi (e.g., IEEE 802.15.11), communication incorporating all or any portion of IEEE 802 or similar communication standards, RFID, 3G or 4G communication, Backscatter communication, light communication, audio/sound communication, harvesting protocol communication (e.g., a metadata harvesting protocol). Other communications protocols or combinations of communications protocols (e.g., a Bluetooth/Mesh combined protocol) can be employed. Additionally or alternatively an acoustic or optical broadcasting is useful.

In a further embodiment, a kit comprising a multitude of absorbent articles and a detector device, which comprises a housing and a connector, such that the detector device can be connected to any one of the absorbent articles is also provided. The absorbent articles and the detector device may each comprise any of the further features described herein. Hence, the detector device can be used on a first absorbent article of the multitude, the absorbent article can be disposed of after use, and the detector device can be re-used on another (fresh) absorbent article.

Figure 2:
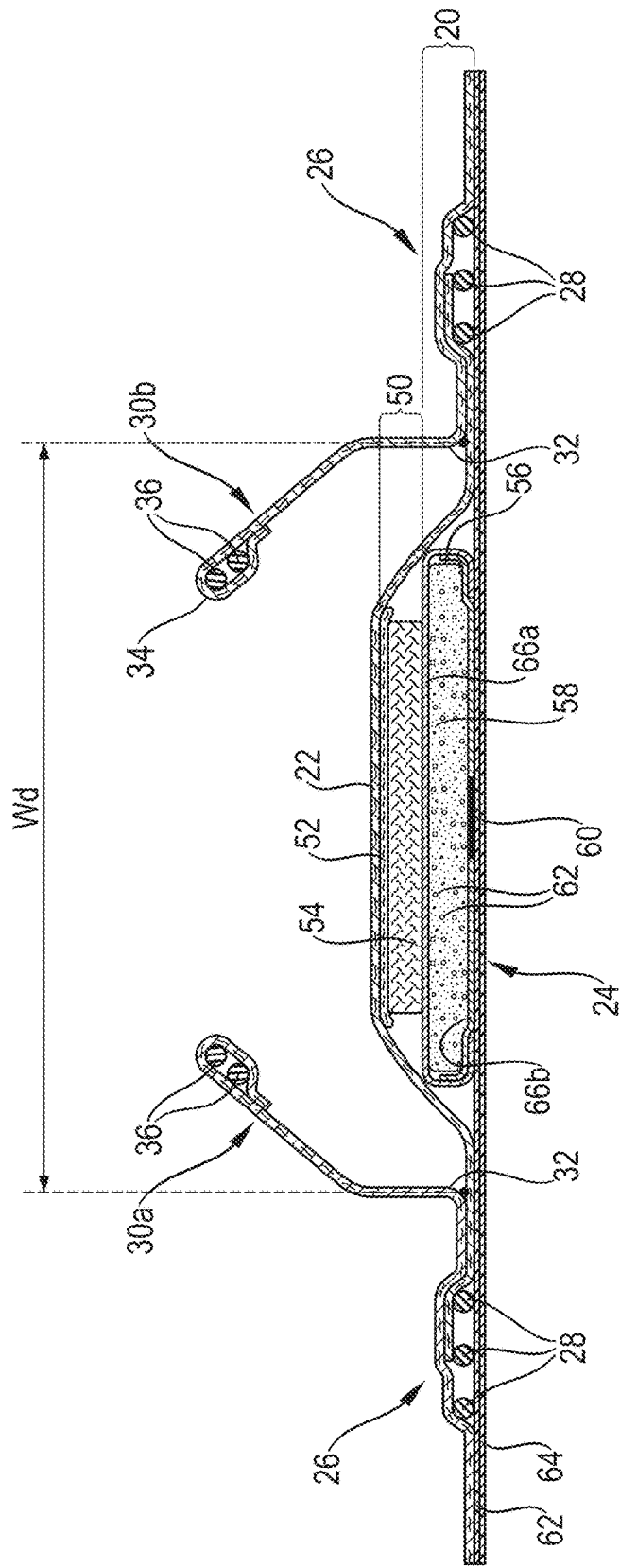
FIG. 2 is a transversal cross-section of the embodiment of FIG. 1 at the crotch area.

An exemplary absorbent article according to one embodiment in the form of an infant diaper 10 is represented in FIGS. 1 and 2.

FIG. 1 is a plan view of the exemplary diaper 10, in a flattened state, with portions of the structure being cut-away to more clearly show the construction of the diaper 10. This diaper 10 is shown for illustration purpose only as many embodiments may use a wide variety of diapers or other absorbent articles. The diaper extends from a front edge 12 to a longitudinally opposed rear edge 14. It comprises left side edge 16 and transversally opposed right side edge 18. The diaper 10 comprises an absorbent core which is positioned between topsheet 22, which is at least partially liquid permeable and backsheet 24, which is essentially impermeable to liquid.

In FIG. 1 "X" denotes a transversal access through the geometrical center of the diaper, and axis "Y" denotes the longitudinal direction. The area A denotes the front area of the diaper as seen in the longitudinal direction and C denotes the rear area of the diaper as seen in the longitudinal direction, and B denotes the central area or crotch area positioned between area A and area B, in the longitudinal direction. L denotes the length of the diaper from the front edge 12 to rear edge 14 as measured in the longitudinal direction.

The article comprises a crotch point P defined herein as the point placed on the longitudinal axis at a distance of two fifth (⅖) of L starting from the front edge 12 of the diaper 10.

The absorbent article comprises an indication means 60, which can take the form of a small sheet of material or patch. As shown, a rectangular form is useful. The indication means 60 can be arranged in the front area A, the central area B or the rear area C of the diaper. It is often useful to range the indication means 60 in the central area B or in the front area A. As shown, it can be useful to provide the indication means 60 towards the front of the crotch point P.

The diaper 10 further comprises gasketing cuffs 26 for maintaining a tight fit of the diaper 10 to the wearer, when the diaper 10 is worn. The gasketing cuffs 26 comprise elastics 28 for maintaining the tight fit, which helps to avoid leakage.

The diaper 10 further comprises barrier leg cuffs 30 on each side of the diaper. Barrier leg cuffs comprise proximal edges 32a and 32b, which are adjacent to topsheet 22. Opposed to the respective proximal edges, the barrier leg cuffs 30 comprise distal edges 34a and 34b, respectively. In the area of the distal edges 34, further elastics 36a provided, while a portion of the distal edges 34 of the barrier leg cuffs 30 can be attached to components of the diaper 10, such as the topsheet 22, it is preferred that the barrier leg cuffs 30 also comprise unattached areas of the distal edges, herein referred to as free flaps 38. The respective free flaps 38 are typically provided in the central zone of the diaper 10.

The diaper 10 further comprises the fastening system, for fastening the diaper to the body of a wearer. This fastening system comprises two back ears 40, which comprise adhesive tapes 42. The adhesive tapes 42 can be attached to landing zone 44. In the front area, the diaper comprises front ears 46. As described below, for other embodiments other fastening systems can be useful, including mechanical fasteners and including fastening systems comprising more than two, for example for IS.

The core can optionally comprise areas, where there is a reduced amount of absorbent material or no absorbent material. These areas are referred to as channels.

FIG. 2 is transversal cross-section of the embodiment of FIG. 1 and readily shows other structural elements of the diaper. As shown in this figure, the diaper comprises an acquisition-distribution system 50. This acquisition-distribution system comprises acquisition layer 52, which first receives liquid, and distribution layer 54 underneath acquisition layer 52.

The absorbent core 20 comprises a core layer 56. This core layer can comprise particular material, such as super absorbent particles, herein also referred to SAP. Between the core layer 56 and the backsheet 24 the indication means 60 can be arranged. As shown in FIG. 2 the backsheet 24 can comprise and inner backsheet layer 62 (which is oriented towards the core 20) and an outer backsheet layer 64, which is generally oriented towards the garments of a wearer. As shown in FIG. 2, in accordance with this particular embodiment, the indicator 60 can be provided above the inner backsheet layer and below the core wrap, more precisely, below the portion of the core wrap 66 which is oriented towards the backsheet 24.

Figure 3:
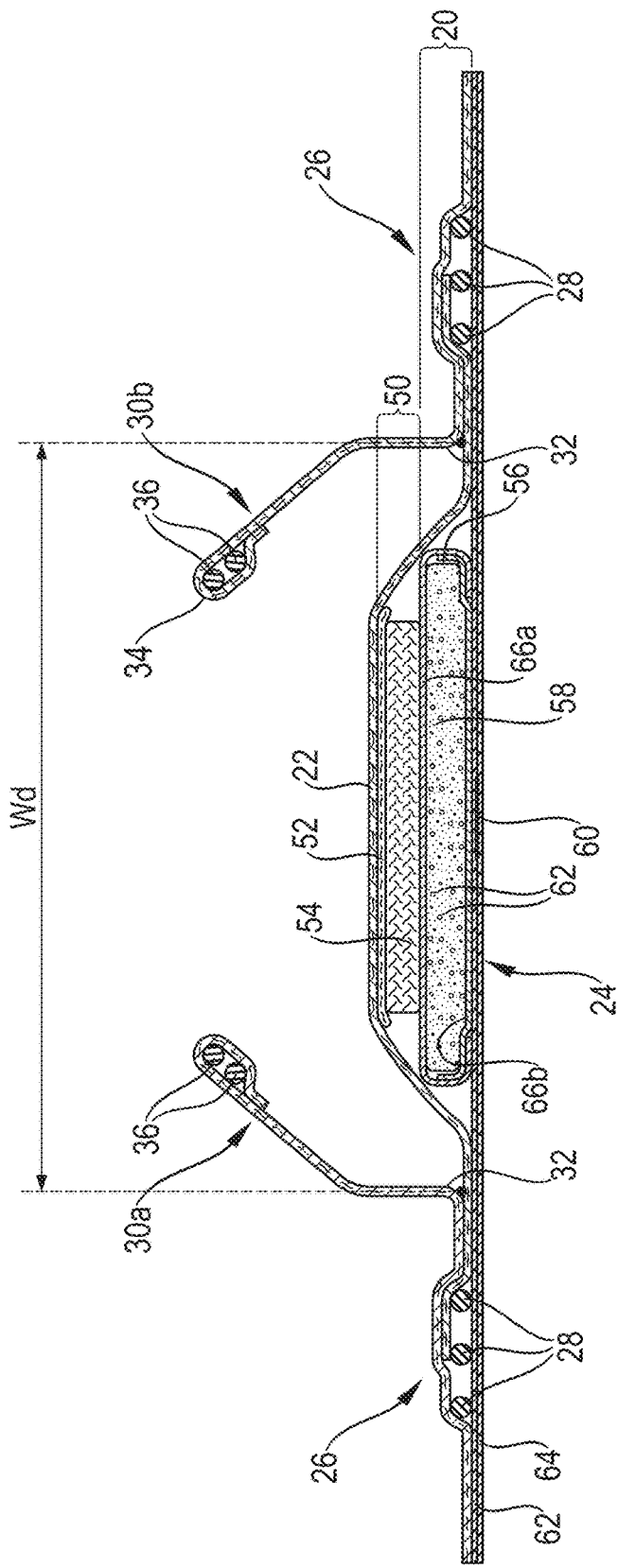
FIG. 3 is a corresponding transversal cross-section of another embodiment of an absorbent article.

FIG. 3 shows another example embodiment of an absorbent article. This embodiment resembles that shown in FIGS. 1 and 2. However, the indicator 60 is arranged here between the inner backsheet layer 62 and the outer backsheet layer 64.

Figure 4:
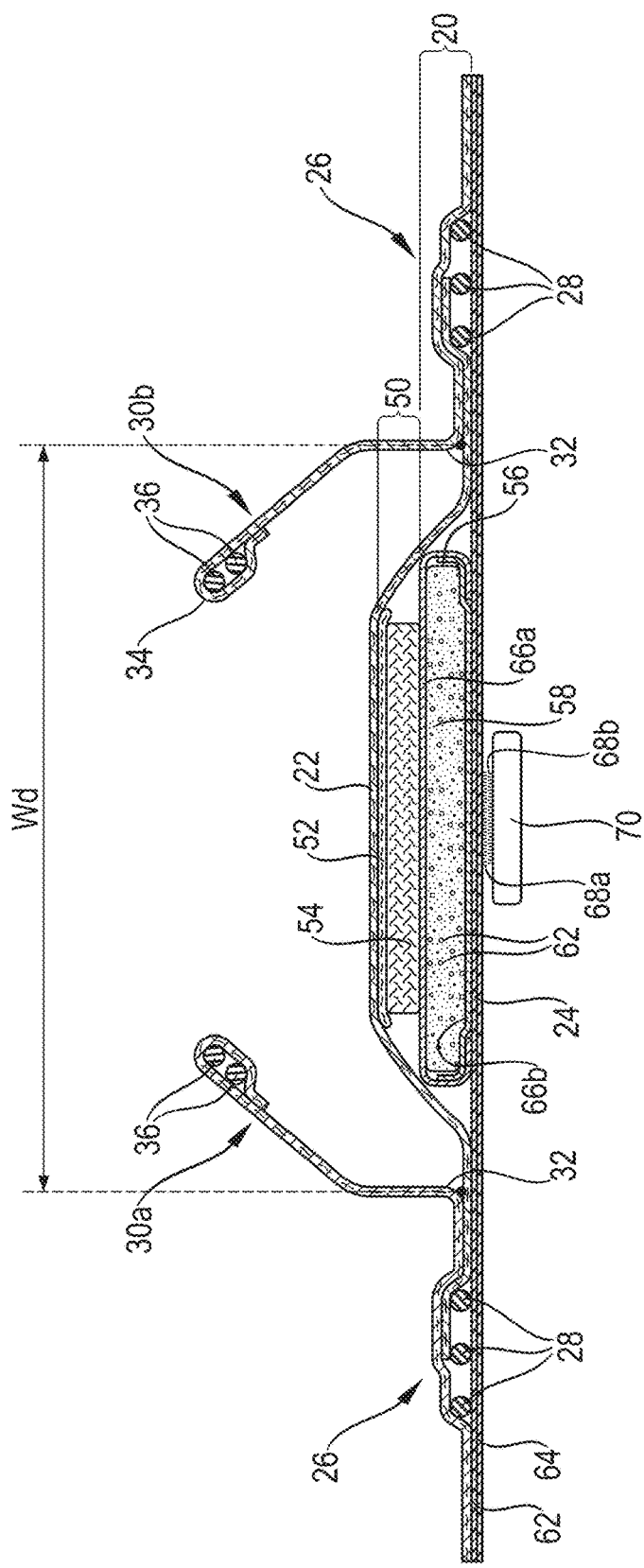
FIG. 4 is a further corresponding transversal cross-section of an embodiment of the present invention.

FIG. 4 shows another example embodiment of an absorbent article. For the embodiment shown in FIG. 2 the absorbent article is shown together with detector device 70. As shown, detector device 70 can take the form of a small pod which can have generally rectangular cross sections. The detector device 70 can be attached to the backsheet 24 of the diaper 10 by a mechanical fastener 68. In one embodiment, for example, the mechanical fastener comprises a first component and a second component. The first component can be attached to backsheet 24 and the second component can be attached to detector device 70. The two components interact with each other, for example hook and loop fasteners can be used. The respective component can be adhesively joined to the backsheet and to the detector device 70, respectively.

The article may also comprise elasticized gasketing cuffs 26 joined to the chassis of the absorbent article, typically via the topsheet and/or backsheet, and substantially planar with the chassis of the diaper.

The Figures also show typical taped diaper components such as a fastening system comprising adhesive tabs 42 attached towards the back edge of the article and cooperating with a landing zone 44 on the front of the article. The absorbent article may also comprise other typical elements, which are not represented, such as a back elastic waist feature, a front elastic waist feature, transverse barrier cuff(s), a lotion application, etc.

The topsheet 22, the backsheet 24, the absorbent core 20 and the other article components may be assembled in a variety of well known configurations, in particular by gluing or heat embossing. Exemplary diaper configurations are described generally in U.S. Pat. Nos. 3,860,003, 5,221,274, 5,554,145, 5,569,234, 5,580,411, and 6,004,306. The absorbent article is preferably thin. The caliper at the crotch point P of the article may be for example from 4.0 mm to 12.0 mm, in particular from 6.0 mm to 10.0 mm, as measured with a suitable caliper test, for example the Absorbent Article Caliper Test disclosed in EP 2 740 450 A1 (Applicant: The Procter & Gamble Company).

These and other components of the articles will now be discussed in more details.

Topsheet 22

The topsheet 22 is the part of the absorbent article that is directly in contact with the wearer's skin. The topsheet 22 can be joined to the backsheet 24, the core 20 and/or any other layers as is known in the art. Usually, the topsheet 22 and the backsheet 24 are joined directly to each other in some locations (e.g. on or close to the periphery of the article) and are indirectly joined together in other locations by directly joining them to one or more other elements of the diaper 10.

The topsheet 22 is preferably compliant, soft-feeling, and non-irritating to the wearer's skin. Further, at least a portion of the topsheet 22 is liquid permeable, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers or filaments (e.g., polyester or polypropylene or bicomponent PE/PP fibers or mixtures thereof), or combinations thereof, e.g. a combination of natural and synthetic fibers. A combination of materials can be achieved by combining at least two materials by means of needle punching, ultra-sonic bonding, ring rolling, embossing, gluing or other types of mechanical entanglement. The resulting material may maintain a dual/multiple layer structure, but may also loose a structure of distinguishable layers after such process steps. It can also be useful to provide a formed film patch underneath the topsheet.

If the topsheet 22 includes fibers, the fibers may be spunbond, carded, wet-laid, meltblown, hydroentangled, or otherwise processed as is known in the art, in particular spunbond PP nonwoven. A suitable topsheet comprising a web of staple-length polypropylene fibers is manufactured by Veratec, Inc., a Division of International Paper Company, of Walpole, Mass. under the designation P-8.

The topsheet 22 may comprise one or more apertures to ease penetration of exudates therethrough, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" from the article is increased. Typically, the total area of the apertures at the surface of a diaper may have an area of between about 10 mm$^2$ and about 50 mm$^2$, in particular between about 15 mm$^2$ and 35 mm$^2$. Examples of apertured topsheet are disclosed in U.S. Pat. No. 6,632,504, assigned to BBA NONWO-VENS SIMPSONVILLE. WO2011/163582 also discloses suitable colored topsheet having a basis weight of from 12 to 18 gsm and comprising a plurality of bonded points. Each of the bonded points has a surface area of from 2 mm$^2$ to 5 mm$^2$ and the cumulated surface area of the plurality of bonded points is from 10 to 25% of the total surface area of the topsheet.

Typical diaper topsheets have a basis weight of from about 10 to about 21 gsm, in particular between from about 12 to about 18 gsm but other basis weights are possible.

Backsheet 24

The backsheet 24 is generally that portion of the diaper 10 positioned adjacent the garment-facing surface of the absorbent core 20 and which prevents the exudates absorbed and contained therein from soiling articles such as bedsheets and undergarments. The backsheet 24 is typically impermeable to liquids (e.g. urine). The backsheet may for example be or comprise a thin plastic film such as a thermoplastic film having a thickness of about 0.012 mm to about 0.051 mm. Exemplary backsheet films include those manufactured by Tredegar Corporation, based in Richmond, Va., and sold under the trade name CPC2 film. Other suitable backsheet materials may include breathable materials which permit vapors to escape from the diaper 10 while still preventing exudates from passing through the backsheet 24. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va., and sold under the designation EXAIRE, and monolithic films such as manufactured by Clopay Corporation, Cincinnati, Ohio under the name HYTREL blend P18-3097. Some breathable composite materials are described in greater detail in PCT Application No. WO 95/16746 published on Jun. 22, 1995 in the name of E. I. DuPont; U.S. Pat. No. 5,938,648 to LaVon et al., U.S. Pat. No. 4,681,793 to Linman et al., U.S. Pat. No. 5,865,823 to Curro; and U.S. Pat. No. 5,571,096 to Dobrin et al, U.S. Pat. No. 6,946,585B2 to London Brown.

The backsheet 24 may be joined to the topsheet 22, the absorbent core 20 or any other element of the diaper 10 by any attachment means known in the art. Suitable attachment means are described above with respect to means for joining the topsheet 22 to other elements of the diaper 10. For example, the attachment means may include a uniform continuous layer of adhesive, a patterned layer of adhesive, or an array of separate lines, spirals, or spots of adhesive. Suitable attachment means comprises an open pattern network of filaments of adhesive as disclosed in U.S. Pat. No. 4,573,986. Other suitable attachment means include several lines of adhesive filaments which are swirled into a spiral pattern, as is illustrated by the apparatus and methods shown in U.S. Pat. Nos. 3,911,173, 4,785,996; and 4,842,666. Adhesives which have been found to be satisfactory are manufactured by H. B. Fuller Company of St. Paul, Minn. and marketed as HL-1620 and HL 1358-XZP. Alternatively, the attachment means may comprise heat bonds, pressure bonds, ultrasonic bonds, dynamic mechanical bonds, or any other suitable attachment means or combinations of these attachment means as are known in the art.

Absorbent Core 20

As used herein, the term "absorbent core" refers to the component or components of the article having the most absorbent capacity and comprising an absorbent material and optionally a core wrap enclosing the absorbent material. The term "absorbent core" does not include the acquisition-distribution system or layer or any other component of the article which is not either integral part of the core wrap or placed within the core wrap. The core may consist essentially of, or consist of, a core wrap, absorbent material as defined below and glue enclosed within the core wrap.

The absorbent core 20 of the absorbent article comprises a first core layer 56 and a second core layer 58. As explained, the absorbent article might comprise and acquisition distribution system, which will typically consist of one or more layers. Most typically, the layers are arranged above the core layer. Hence, a number of layers can be arranged between the topsheet and the backsheet. The skilled person will usually have no difficulty in distinguishing between these layers. In case of doubt, a core layer can be identified as being a layer which is generally less permeable than a layer forming part of the acquisition-/distribution-system.

Permeability generally refers to the quality of a porous material that causes it to a lower liquid or gases to pass through it. Hence, the layers of the acquisition distribution system should generally be more permeable than the layers of the core system as these layers are meant to distribute liquid to the absorbent core, where the liquid is ultimately stored.

The absorbent core can comprise absorbent material with a varying amount of superabsorbent polymers (herein abbreviated as "SAP"), often enclosed within a core wrap. The SAP content can represent from 0% to 80% by weight of the absorbent material contained in the core wrap. Often an SAP content of 20% to 50% by weight of the absorbent material contained in the core wrap is useful. The core wrap is not considered as absorbent material for the purpose of assessing the percentage of SAP in the absorbent core.

By "absorbent material" it is meant a material which has some absorbency property or liquid retaining properties, such as SAP, cellulosic fibers as well as synthetic fibers. Herein, absorbent materials in the form of fibrous absorbent materials have been found to be useful. These fibrous absorbent materials can comprise or consist of natural fibers, e.g. cellulosic fibers as well as synthetic fibers. Typically, glues used in making absorbent cores have no absorbency properties and are not considered as absorbent material.

The SAP content may be higher than 30%, for example at least 40%, at least 50%, at least 80% of the weight of the absorbent material contained within the core wrap. The absorbent material may in particular embodiments comprise from 10 to 70, for example 30 to 60 weight percent of natural or synthetic fibers.

The absorbent core may comprise a generally planar top edge and a generally planar bottom edge. In some embodiments, the absorbent material will be advantageously distributed in higher amount towards the front edge than towards the rear edge as more absorbency is required at the front. In other embodiments, typically embodiments for other uses of an absorbent article, such as care of elderly incontinent people versus care of babies, the absorbent material will be advantageously distributed in higher amount towards the rear edge than towards the front edge as more absorbency is required at the rear area.

The core wrap may be formed by two separate sheets of nonwoven material which may be at least partially sealed along the edges of the absorbent core. The core wrap may be at least partially sealed along its front edge, back edge and two longitudinal edges so that substantially no absorbent material leaks out of the absorbent core wrap.

The absorbent core of the absorbent article may further comprise adhesive for example to help immobilizing the SAP within the core wrap and/or to ensure integrity of the core wrap, in particular when the core wrap is made of two or more substrates. Such an adhesive can be provided in the form of fibrous thermoplastic adhesive material.

The fibrous thermoplastic adhesive material may be at least partially in contact with the superabsorbent material in the land areas and at least partially in contact with the substrate layer in the junction areas. This imparts an essentially three-dimensional structure to the fibrous layer of thermoplastic adhesive material, which in itself is essentially a two-dimensional structure of relatively small thickness, as compared to the dimension in length and width directions. Thereby, the fibrous thermoplastic adhesive material may provide cavities to cover the absorbent material in the land area, and thereby immobilizes this absorbent material.

The thermoplastic adhesive material may comprise, in its entirety, a single thermoplastic polymer or a blend of thermoplastic polymers, having a softening point, as determined by the ASTM Method D-36-95 "Ring and Ball", in the range between 50° C. and 300° C., and/or the thermoplastic adhesive material may be a hotmelt adhesive comprising at least one thermoplastic polymer in combination with other thermoplastic diluents such as tackifying resins, plasticizers and additives such as antioxidants.

Superabsorbent Polymer (SAP)

Superabsorbent material, herein also referred to as superabsorbent polymer material, superabsorbent polymers or SAP, refers to absorbent materials which are cross-linked polymeric materials that can absorb at least 10 times their weight of an aqueous 0.9% saline solution as measured using the Centrifuge Retention Capacity (CRC) test (EDANA method WSP 241.2-05E). The SAP used may in particular have a CRC value of more than 20 g/g, or more than 24 g/g, or of from 20 to 50 g/g, or from 20 to 40 g/g, or 24 to 30 g/g. The SAP useful in example absorbent articles may include a variety of water-insoluble, but water-swellable polymers capable of absorbing large quantities of fluids.

The superabsorbent polymer can be in particulate form so as to be flowable in the dry state. Typical particulate absorbent polymer materials are made of poly(meth)acrylic acid polymers. However, e.g. starch-based particulate absorbent polymer material may also be used, as well polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. The superabsorbent polymer may be polyacrylates and polyacrylic acid polymers that are internally and/or surface cross-linked.

The SAP useful for example embodiments of absorbent articles may be of numerous shapes. The term "particles" refers to granules, fibers, flakes, spheres, powders, platelets and other shapes and forms known to persons skilled in the art of superabsorbent polymer particles. In some embodiments, the SAP particles can be in the shape of fibers, i.e. elongated, acicular superabsorbent polymer particles. In those embodiments, the superabsorbent polymer particles fibers have a minor dimension (i.e. diameter of the fiber) of less than about 1 mm, usually less than about 500 µm, and preferably less than 250 µm down to 50 µm. The length of the fibers is preferably about 3 mm to about 100 mm. The fibers can also be in the form of a long filament that can be woven.

Typically, SAP are spherical-like particles. In contrast to fibers, "spherical-like particles" have a longest and a smallest dimension with a particulate ratio of longest to smallest particle dimension in the range of 1-5, where a value of 1 would equate a perfectly spherical particle and 5 would allow for some deviation from such a spherical particle. The superabsorbent polymer particles may have a particle size of less than 850 µm, or from 50 to 850 µm, preferably from 100 to 710 µm, more preferably from 150 to 650 µm, as measured according to EDANA method WSP 220.2-05. SAP having a relatively low particle size help to increase the surface area of the absorbent material which is in contact with liquid exudates and therefore support fast absorption of liquid exudates.

The SAP may have a particle sizes in the range from 45 µm to 4000 µm, more specifically a particle size distribution within the range of from 45 µm to about 2000 µm, or from about 100 µm to about 1000, 850 or 600 µm. The particle size distribution of a material in particulate form can be determined as it is known in the art, for example by means of dry sieve analysis (EDANA 420.02 "Particle Size distribution).

In some embodiments herein, the superabsorbent material is in the form of particles with a mass medium particle size up to 2 mm, or between 50 microns and 2 mm or to 1 mm, or preferably from 100 or 200 or 300 or 400 or 500 µm, or to 1000 or to 800 or to 700 µm; as can for example be measured by the method set out in for example EP-A-0,691,133. In some embodiments of an absorbent article, the superabsorbent polymer material is in the form of particles whereof at least 80% by weight are particles of a size between 50 µm and 1200 µm and having a mass median particle size between any of the range combinations above. In addition, or in another embodiment of an absorbent article, the particles are essentially spherical. In yet another or additional embodiment of an absorbent article, the superabsorbent polymer material has a relatively narrow range of particle sizes, e.g. with the majority (e.g. at least 80% or preferably at least 90% or even at least 95% by weight) of particles having a particle size between 50 µm and 1000 µm, preferably between 100 µm and 800 µm, and more preferably between 200 µm and 600 µm.

The surface of the SAP may be coated, for example, with a cationic polymer. Preferred cationic polymers can include polyamine or polyimine materials. In some embodiments, the SAP may be coated with chitosan materials such as those disclosed in U.S. Pat. No. 7,537,832 B2. In some other embodiments, the SAP may comprise mixed-bed Ion-Exchange absorbent polymers such as those disclosed in WO 99/34841 and WO 99/34842.

The absorbent core will typically comprise only one type of SAP, but it is not excluded that a blend of SAPs may be used. The fluid permeability of a superabsorbent polymer can be quantified using its Urine Permeability Measurement (UPM) value, as measured in the test disclosed European patent application number EP12174117.7. The UPM of the SAP may for example be of at least $10\times10^{-7}$ cm$^3$·sec/g, or at least $30\times10^{-7}$ cm$^3$·sec/g, or at least $50\times10^{-7}$ cm$^3$·sec/g, or more, e.g. at least 80 or $100\times10^{-7}$ cm$^3$·sec/g. The flow characteristics can also be adjusted by varying the quantity and distribution of the SAP used in the second absorbent layer.

For most absorbent articles, the liquid discharge occurs predominately in the front half of the article, in particular for diaper. The front half of the article (as defined by the region between the front edge and a transversal line placed at a distance of half L from the front or back edge may therefore comprise most of the absorbent capacity of the core. Thus, at least 60% of the SAP, or at least 65%, 70%, 75% or 80% of the SAP may be present in the front half of the absorbent article, the remaining SAP being disposed in the back half of the absorbent article.

The total amount of SAP present in the absorbent core may also vary according to expected usage. Diapers for newborns may require less SAP than infant or adult incontinence diapers. The amount of SAP in the core may be for example comprised from about 2 to 60 g, in particular from 5 to 50 g or 10 to 40 g. The average SAP basis weight within the (or "at least one", if several are present) deposition area of the SAP may be for example of at least 50, 100, 200, 300, 400, 500 or more g/m$^2$. The areas of the channels present in the absorbent material deposition area, if any, are deduced from the absorbent material deposition area to calculate this average basis weight.

Core Wrap 66

The optional core wrap may be made of a single substrate folded around the absorbent material, or may advantageously comprise two (or more) substrates which are attached to another. Typical attachments are the so-called C-wrap and/or sandwich wrap. In a C-wrap, as exemplarily shown in FIG. 2, the longitudinal and/or transversal edges of one of the substrate are folded over the other substrate to form flaps. These flaps are then bonded to the external surface of the other substrate, typically by gluing.

If the core wrap comprises a first substrate 66a and a second substrate 66b these may be made of the same type of material, or may be made of different materials or one of the substrate may be treated differently than the other to provide it with different properties. As the polymers used for nonwoven production are inherently hydrophobic, they are preferably coated with hydrophilic coatings if placed on the fluid receiving side of the absorbent core. It is advantageous that the top side of the core wrap, i.e. the side placed closer to the wearer in the absorbent article, be more hydrophilic than the bottom side of the core wrap. A possible way to produce nonwovens with durably hydrophilic coatings is via applying a hydrophilic monomer and a radical polymerization initiator onto the nonwoven, and conducting a polymerization activated via UV light resulting in monomer chemically bound to the surface of the nonwoven. An alternative possible way to produce nonwovens with durably hydrophilic coatings is to coat the nonwoven with hydrophilic nanoparticles, e.g. as described in WO 02/064877.

Barrier Leg Cuffs 30

The absorbent article comprises a pair of barrier leg cuffs 30. The barrier leg cuffs can be formed from a piece of material, typically a nonwoven, which is partially bonded to the rest of the article so that a portion of the material, the barrier leg cuffs, can be partially raised away and stand up from the plane defined by the topsheet when the article is pulled flat as shown e.g. in FIG. 1. The barrier leg cuffs can provide improved containment of liquids and other bodily exudates approximately at the junction of the torso and legs of the wearer. The barrier leg cuffs extend at least partially between the front edge and the back edge of the diaper on opposite sides of the longitudinal axis and are at least present at the level of the crotch point (P). The barrier leg cuffs are delimited by a proximal edge 32 joined to the rest of the article, typically the topsheet and/or the backsheet, and a free terminal edge 66, which is intended to contact and form a seal with the wearer's skin. The barrier leg cuffs are joined at the proximal edge 32 with the chassis of the article by a bond 33 which may be made for example by gluing, fusion bonding or combination of known bonding means. The bond 33 at the proximal edge 32 may be continuous or intermittent. The side of the bond 33 closest to the raised section of the leg cuffs delimits the proximal edge 32 of the standing up section of the leg cuffs. The distance between the inner sides of these bond 33 define the dry and wet width of the article at this level for the purpose of RCWR test (see below).

The barrier leg cuffs can be integral with the topsheet or the backsheet, or more typically be formed from a separate material joined to the rest of the article. Typically the material of the barrier leg cuffs may extend through the whole length of the diapers but is "tack bonded" to the topsheet towards the front edge and back edge of the article so that in these sections the barrier leg cuff material remains flush with the topsheet. Each barrier leg cuff 30 may comprise one, two or more elastic 36 close to this free distal edge 34 to provide a better seal.

In addition to the barrier leg cuffs 30, the article may comprise gasketing cuffs 26, which are joined to the chassis of the absorbent, article, in particular the topsheet and/or the backsheet and are placed transversely outwardly relative to the barrier leg cuffs. The gasketing cuffs can provide a better seal around the thighs of the wearer. Usually each gasketing leg cuff will comprise one or more elastic string or elastic element comprised in the chassis of the diaper for example between the topsheet and backsheet in the area of the leg openings.

U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. describe disposable diapers having "stand-up" elasticized flaps (barrier leg cuffs) which improve the containment of the leg regions. U.S. Pat. Nos. 4,695,278 and 4,795,454 issued to Lawson and to Dragoo respectively, describe disposable diapers having dual cuffs, including gasketing cuffs and barrier leg cuffs. All or a portion of the barrier leg and/or gasketing cuffs may be treated with a lotion.

Acquisition-Distribution System 50

Embodiments of the absorbent articles may comprise an acquisition-distribution layer or system 50 (herein "ADS"). The function of the ADS is to quickly acquire the fluid and distribute it to the absorbent core in an efficient manner. The ADS may comprise one, two or more layers, which may form a unitary layer or remain discrete layers which may be attached to each other. In the examples below, the ADS comprises two layers: a distribution layer 54 and an acquisition layer 52 disposed between the absorbent core and the topsheet, but embodiments of absorbent articles are not restricted to this example.

Typically, the ADS will not comprise SAP as this may slow the acquisition and distribution of the fluid. The prior art discloses many type of acquisition-distribution system, see for example WO2000/59430 (Daley), WO95/10996 (Richards), U.S. Pat. No. 5,700,254 (McDowall), WO02/067809 (Graef). The ADS may comprise, although not necessarily, two layers: a distribution layer and an acquisition layer, which will now be exemplified in more details.

Distribution Layer 54

The distribution layer may for example comprise at least 50% by weight of cross-linked cellulose fibers. The cross-linked cellulosic fibers may be crimped, twisted, or curled, or a combination thereof including crimped, twisted, and curled. This type of material has been used in the past in disposable diapers as part of an acquisition system, for example US 2008/0312622 A1 (Hundorf). The cross-linked cellulosic fibers provide higher resilience and therefore higher resistance to the first absorbent layer against the compression in the product packaging or in use conditions, e.g. under baby weight. This provides the core with a higher void volume, permeability and liquid absorption, and hence reduced leakage and improved dryness.

The distribution layer comprising cross-linked cellulose fibers of the absorbent article may comprise other fibers, but this layer may advantageously comprise at least 50%, or 60%, or 70%, or 80%, or 90% or even up to 100%, by weight of the layer, of cross-linked cellulose fibers (including the cross-linking agents). Examples of such mixed layer of cross-linked cellulose fibers may comprise about 70% by weight of chemically cross-linked cellulose fibers, about 10% by weight polyester (PET) fibers, and about 20% by weight untreated pulp fibers. In another example, the layer of cross-linked cellulose fibers may comprise about 70% by weight chemically cross-linked cellulose fibers, about 20% by weight lyocell fibers, and about 10% by weight PET fibers. In another example, the layer may comprise about 68% by weight chemically cross-linked cellulose fibers, about 16% by weight untreated pulp fibers, and about 16% by weight PET fibers. In another example, the layer of cross-linked cellulose fibers may comprise from about 90-100% by weight chemically cross-linked cellulose fibers.

The distribution layer 54 may be a material having a water retention value of from 25 to 60, preferably from 30 to 45, measured as indicated in the procedure disclosed in U.S. Pat. No. 5,137,537.

The distribution layer may typically have an average basis weight of from 30 to 400 g/m$^2$, in particular from 100 to 300 g/m$^2$. The density of the distribution layer may vary depending on the compression of the article, but may be of between 0.03 to 0.15 g/cm$^3$, in particular 0.08 to 0.10 g/cm$^3$ measured at 0.30 psi (2.07 kPa).

Acquisition Layer 52

The ADS may comprise an acquisition layer 52. The acquisition layer may be disposed between the distribution layer 54 and topsheet 22. The acquisition layer 52 may typically be or comprise a non-woven material, for example a SMS or SMMS material, comprising a spunbonded, a melt-blown and a further spunbonded layer or alternatively a carded chemical-bonded nonwoven. The non-woven material may in particular be latex bonded. Exemplary upper acquisition layers 52 are disclosed in U.S. Pat. No. 7,786, 341. Carded, resin-bonded nonwovens may be used, in particular where the fibers used are solid round or round hollow PET staple fibers (50/50 or 40/60 mix of 6 denier and 9 denier fibers). An exemplary binder is a butadiene/styrene latex. Non-wovens have the advantage that they can be manufactured outside the converting line and stored and used as a roll of material.

Further useful non-wovens are described in U.S. Pat. No. 6,645,569 to Cramer et al., U.S. Pat. No. 6,863,933 to Cramer et al., U.S. Pat. No. 7,112,621 to Rohrbaugh et al., and co patent applications US 2003/148684 to Cramer et al. and US 2005/008839 to Cramer et al.

The acquisition layer 52 may be stabilized by a latex binder, for example a styrene-butadiene latex binder (SB latex). Processes for obtaining such lattices are known, for example, from EP 149 880 (Kwok) and US 2003/0105190 (Diehl et al.). In certain embodiments, the binder may be present in the acquisition layer 52 in excess of about 12%, about 14% or about 16% by weight. SB latex is available under the trade name GENFLO™ 3160 (OMNOVA Solutions Inc.; Akron, Ohio).

A further acquisition layer may be used in addition to a first acquisition layer described above. For example a tissue layer may be placed between the first acquisition layer and the distribution layer. The tissue may have enhanced capillarity distribution properties compared to the acquisition layer described above. The tissue and the first acquisition layer may be of the same size or may be of different size, for example the tissue layer may extend further in the back of the absorbent article than the first acquisition layer. An example of hydrophilic tissue is a 13-15 gsm high wet strength made of cellulose fibers from supplier Havix.

Fastening System

The absorbent article may include a fastening system. The fastening system can be used to provide lateral tensions about the circumference of the absorbent article to hold the absorbent article on the wearer as is typical for taped diapers. This fastening system is not necessary for training pant article since the waist region of these articles is already bonded. The fastening system usually comprises a fastener such as tape tabs (also referred to as adhesive tabs), hook and loop fastening components, interlocking fasteners such as tabs & slots, buckles, buttons, snaps, and/or hermaphroditic fastening components, although any other known fastening means are generally acceptable. A landing zone is normally provided on the front waist region for the fastener to be releasably attached. Some exemplary surface fastening systems are disclosed in U.S. Pat. Nos. 3,848,594, 4,662,875, 4,846,815, 4,894,060, 4,946,527, 5,151,092 and 5,221,274 issued to Buell. An exemplary interlocking fastening system is disclosed in U.S. Pat. No. 6,432,098. The fastening system may also provide a means for holding the article in a disposal configuration as disclosed in U.S. Pat. No. 4,963,140 issued to Robertson et al.

The fastening system may also include primary and secondary fastening systems, as disclosed in U.S. Pat. No. 4,699,622 to reduce shifting of overlapped portions or to improve fit as disclosed in U.S. Pat. Nos. 5,242,436, 5,499,978, 5,507,736, and 5,591,152.

Back Ears 40 and Front Ears 46

The absorbent article may comprise front ears 46 and back ears 40 as is known in the art. The ears can be integral part of the chassis, for example formed from the topsheet and/or backsheet as side panel. Alternatively, as represented on FIG. 1, they may be separate elements attached by gluing and/or heat embossing or pressure bonding. The back ears 40 are advantageously stretchable to facilitate the attachment of the adhesive tabs 42 on the landing zone 44 and maintain the taped diapers in place around the wearer's waist. The back ears 40 may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

Elastic Waist Feature

The absorbent article may also comprise at least one elastic waist feature (not represented) that helps to provide improved fit and containment. The elastic waist feature is generally intended to elastically expand and contract to dynamically fit the wearer's waist. The elastic waist feature preferably extends at least longitudinally outwardly from at least one waist edge of the absorbent core 20 and generally forms at least a portion of the end edge of the absorbent article. Disposable diapers can be constructed so as to have two elastic waist features, one positioned in the front waist region and one positioned in the back waist region. The elastic waist feature may be constructed in a number of different configurations including those described in U.S. Pat. Nos. 4,515,595, 4,710,189, 5,151,092 and 5,221,274.

Relations Between the Layers

Typically, adjacent layers and components will be joined together using conventional bonding method such as adhesive coating via slot coating or spraying on the whole or part of the surface of the layer, or thermo-bonding, or pressure bonding or combinations thereof. This bonding is not represented in the Figures (except for the bonding by bonds 33 between the raised elements of the barrier leg cuffs 30 with the topsheet 22) for clarity and readability but bonding between the layers of the article should be considered to be present unless specifically excluded. Adhesives may be typically used to improve the adhesion of the different layers, for example between the backsheet and the core wrap. The glue may be any standard hotmelt glue as known in the art.

If an acquisition layer 52 is present, it may be advantageous that this acquisition layer is larger than or least as large as the distribution layer 54 in the longitudinal and/or transversal dimension. In this way the distribution layer 54 can be deposited on the acquisition layer 52 during the manufacturing process before assembling these layers in the finished article. This simplifies handling, in particular if the acquisition layer is a nonwoven which can be unrolled from a roll of stock material. The distribution layer may also be deposited directly on the absorbent core's upper side of the core wrap or another layer of the article. Also, an acquisition layer 52 larger than the distribution layer allows to directly glue the acquisition layer to the storage core (at the larger areas). This can give increased integrity to the article and better liquid communication.

The absorbent core and in particular its absorbent material deposition area may advantageously be at least as large and long and advantageously at least partially larger and/or longer than the acquisition-distribution system (ADS). This is because the absorbent material in the core can usually more effectively retain fluid and provide dryness benefits across a larger area than the ADS. The absorbent article may have a rectangular SAP layer and a non-rectangular (shaped) ADS. The absorbent article may also have a rectangular (non-shaped) ADS and a rectangular layer of SAP.

The absorbent articles may be made by any conventional methods known in the art. In particular the articles may be hand-made or industrially produced at high speed.

The values indicated herein are measured according to the methods indicated herein below, unless specified otherwise. All measurements are performed at 21±2° C. and 50±20% RH, unless specified otherwise. All samples should be kept at least 24 hours in these conditions to equilibrate before conducting the tests, unless indicated otherwise. All measurements should be reproduced on at least 4 samples and the average value obtained indicated, unless otherwise indicated.

Figure 5:
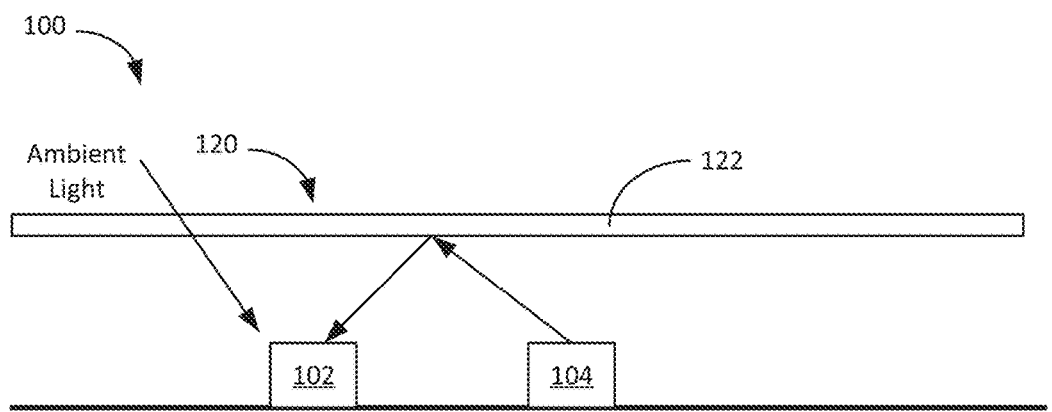
FIG. 5 shows a partial schematic view of an example embodiment of a reusable detector device that may be removably attached externally to a diaper, such as shown in FIG. 4

FIGS. 5A and 5B show partial schematic views of an example embodiment of a reusable detector device 100 that may be removably attached externally to a diaper, such as shown in FIG. 4. In this example embodiment, for example, all electronic components of the detector may be disposed outside the diaper. The detector device 100 is adapted to detect one or more color changes in an indicator 120, such as a color change strip 122, disposed within the diaper. In this particular embodiment, the indicator 120 changes color directly or indirectly in response to presence and/or absence of a bodily exudate within the diaper.

The color change strip 122, for example, may be disposed in the diaper such as shown in FIG. 1 generally along a mid-line of the diaper and extend a predetermined distance in the cross-direction of the diaper. In one particular embodiment, for example, the color change strip 122 is between approximately 4 mm and 15 mm wide, such as approximately 10 mm wide, and between approximately 100 and 300 mm long, such as approximately 100 mm, 150 mm, 200 mm, 250 mm or 300 mm long. The dimensions of the color change strip, however, are merely exemplary and not limiting. The color change strip 122 (or other indicator 120), for example, may include any number of form factors, such as but not limited to one or more stripes, circles, rectangles, dots, designs (e.g., a character or other drawing). The indicator 120 may also be disposed in other locations of the diaper than shown in FIG. 1. Further, where the indicator 120 includes a material (e.g., adhesive, SAP/AGM) that migrates within the diaper or fades as the more bodily exudates are introduced into the diaper, a detection algorithm may maintain a state of wet/soiled once an initial detection has been made. For example, a ratchet or other feature in an algorithm may be used to maintain an indication that bodily exudates have been detected until the diaper has been changed or the detector 100 has been removed from the diaper.

The detector device 100 includes one or more optical (e.g., color) sensors 102 and a light source 104 (e.g., an LED). The optical sensor 102 measures one or more light levels from the indicator 120. In one particular embodiment, for example, the color sensor measures four light levels—clear, red, green and blue—with a sixteen (16) bit resolution. The clear level corresponds to a measure of an overall light intensity and the red, green and blue levels correspond to intensity in the relevant parts of the spectrum from the indicator 120. In this embodiment, the detector device 100 takes multiple measurements with the optical sensor 102. In a first operation, the optical sensor 102 is read without the light source 104 (e.g., the LED) illuminated to determine a background light level. Another reading of the color sensor is taken in another operation with the light source 104 illuminating the color change strip 122 of the indicator 120 to measure the clear, red, green and blue (RGB) light levels. A difference between the two measurements is obtained in a third operation and represents a color of the color change strip 122 of the indicator 120. The clear color level may be used to normalize the RGB values. Fill levels corresponding to one or more intermediate states of the indicator 120 may also be determined, such as from the hue, saturation and brightness (HSB) values in combination with or instead of the RGB values.

The optical sensor 102 may be spaced from the light source 104 so that direct light from the light source 104 is reduced or eliminated at the optical sensor 102. Similarly, too large a spacing between the optical sensor 102 and the light source 104 may reduce the signal strength at the optical sensor 102. In one embodiment, for example, the optical sensor 102 may be spaced at least about 5 mm from the light source 104. In another embodiment, the optical sensor may be spaced at least about 8 mm from the light source 104, at least about 10 mm from the light source 104, between approximately 5 and 20 mm from the light source 104, and between approximately 10 to 15 mm from the light source 104.

In addition to spacing between the optical sensor 102 and the light source 104, other factors may also affect light level measurements of the optical sensor 102. For example, temperature, location of the detector device 100 on the diaper, the type, material and color of a connector (e.g., adhesive, tape, hook and loop, strap and other materials) disposed between the detector device 100 and the indicator 120 disposed within the diaper, orientation of the detector device 100 relative to the indicator 120, orientation of transmit and receive windows of the detector device 100 and the diaper, force of application of the detector device 100 against the diaper (e.g., may affect the distance between the optical sensor 102 and light source 104 of the detector device 100 and the indicator 120 of the diaper in use), ambient light, placement of an attachment zone on the diaper for coupling to the detector device 100 and placement of the detector device 100 relative to the indicator 120 of the diaper (e.g., in a cross-direction) such that the optical sensor 102 detects other components of the diaper disposed near the indicator 120.

In one embodiment, for example, the color change strip 122 changes color in response to a change in pH within the diaper. Swelling of Super Absorbent Polymers (SAP)/Absorbent Gelling Materials (AGM) within the diaper changes the pH of the environment within the diaper. In response to a change in pH, the color change strip 122 changes in color. The color change strip 122, for example, may comprise a pH sensitive glue, such as H9588 glue that is commercially available from Bostik. While a human eye may only be able to distinguish general changes in color, such as a transition from yellow (dry) to blue (wet), an electronic color sensor such as a photodiode can detect intermediate colors as the indicator transitions from a first state to a second state.

Although a pH sensitive color change strip 122 is discussed with respect to an example embodiment, the indicator 120 is not so limited. Rather, the indicator 120 may include any indicator that changes color or other appearance directly or indirectly related to the presence or absence of bodily exudates within the diaper. For example, color change materials that change from no color to one or more colors, from one or more colors to no colors, change colors in other color ranges than the pH sensitive adhesive described herein, materials that change color or appearance based on factors other than pH changes, such as but not limited to, temperature, wetness, odor, enzymes, organic components, inorganic components (e.g., salt level), colored SAP/AGM, mechanical forces (e.g., strain, stretch) or the like.

As discussed with respect to FIG. 4 above, the detector device 100, may include one or more user signal devices, which may include an audio and/or visual indicator such as but not limited to one or more LEDs, LCDs, display screens, lights, speakers or other indicators, that may be used to indicate the presence and/or absence of bodily exudates detected within the diaper.

The detector device 100 may further include a communication module 106 adapted to transmit data from the detector device 100 to a remote device 130, such as for storage and/or presentation to a user. The communication module 106, for example, may include a Bluetooth communication module, a BTLE communication module, a mesh communication module (e.g., IEEE 802.15.4), a WiFi communication module (e.g., IEEE 802.15.11), a communication module incorporating all or any portion of IEEE 802 or similar communication standards, an RFID module, a 3G or 4G communication module, a Backscatter communication module, a light communication module, a sound communication module, a harvesting protocol communication module (e.g., a metadata harvesting protocol communication module. Other communications protocols or combinations of communications protocols (e.g., a Bluetooth/Mesh combined protocol) and mechanisms may also be used.

In one embodiment, for example, a smartphone, tablet, computer or other remote device may be used to receive information from the detector device 100, determine one or more state of the diaper (e.g., presence or absence of one or more bodily exudates) and display information related to the state of the diaper to a user. The remote device may be in direct communication with the detector device and/or be communicatively coupled with detector device (or via an intermediate device) via one or more computer networks, such as the Internet.

Figure 6:
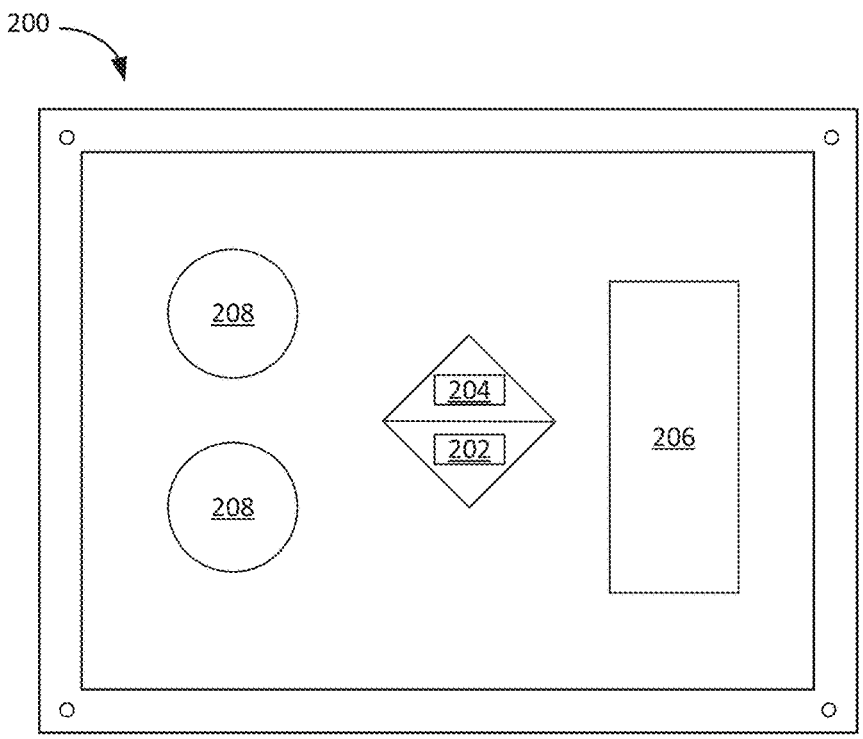
FIG. 6 shows a block diagram of an example implementation of a detector device adapted for removably coupling with one or more diapers.

FIG. 6 shows a block diagram of an example implementation of a detector device 200 adapted for removably coupling with one or more diapers. In this particular embodiment, the detector device 200 includes a color sensor 202, an LED light source 204, a low energy Bluetooth (BTLE) communication module 206 and one or more batteries 208. The batteries 208, for example, may include one or more silver oxide batteries, nickel cadmium batteries, lithium batteries, alkaline batteries, capacitors or other energy storage devices. The batteries 208 may be disposable or rechargeable and provide power to the other components of the detector device 200. In one embodiment, the detector device may further include one or more processors and memory storage for providing processing on the detector device 200.

The communications module 206, for example, may be limited in power and/or duration of transmission to reduce electromagnetic (EM) energy transmitted in close proximity to a wearer of the diaper. The BTLE module 206, for example, may be operated at approximately 2 mW for approximately 0.005% time of the time it is in operation (approximately one transmission per minute).

Figure 7:
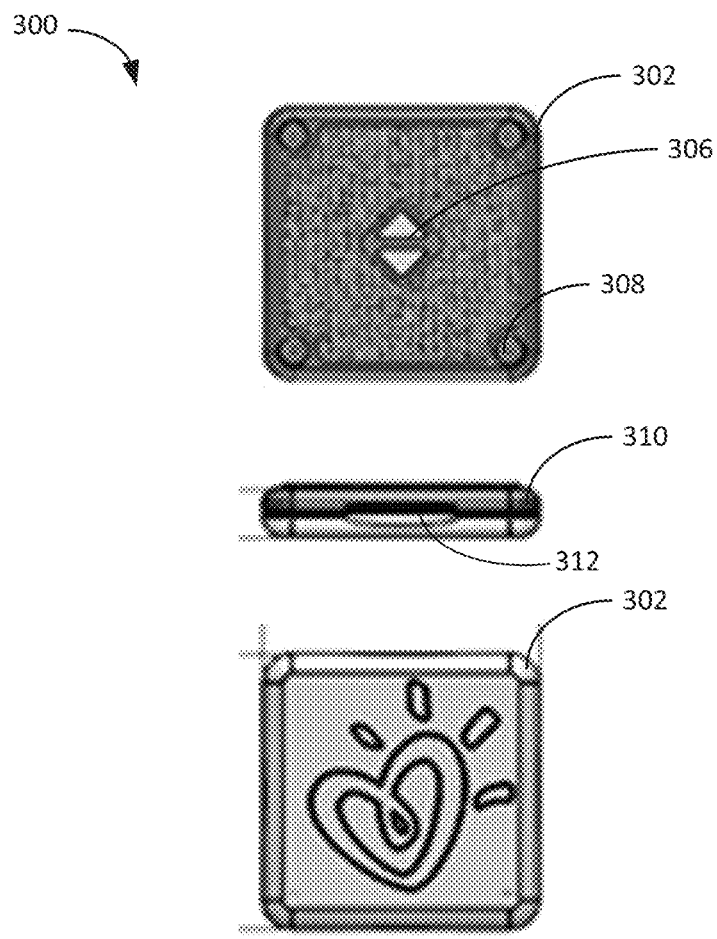
FIG. 7 shows top, bottom and side views of an example embodiment of an exterior of a detector device, such as the one shown in FIG. 6.
Figure 8:
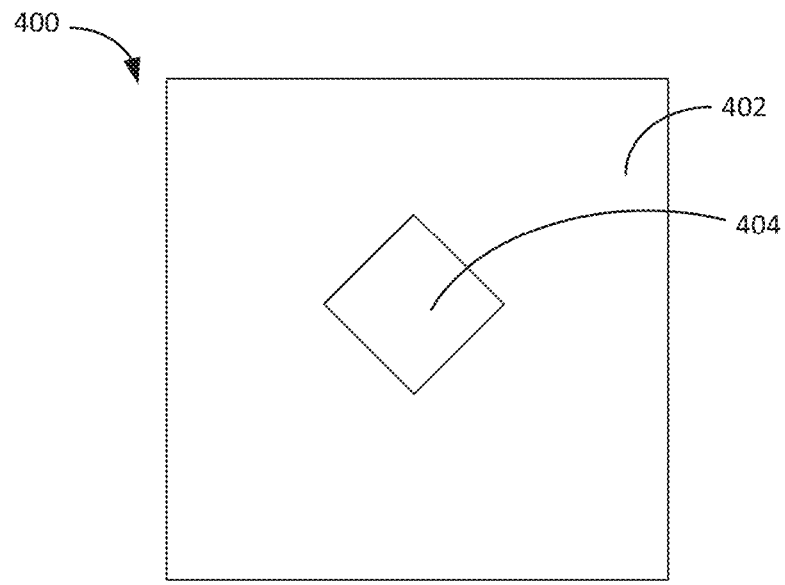
FIG. 8 shows an example embodiment an attachment zone of a diaper exterior adapted for receiving a detector device, such as the detector device shown in FIGS. 6 and 7.

FIG. 7 shows top, bottom and side views of an example embodiment of an exterior of a detector device 300, such as the one shown in FIG. 8. In this embodiment, the top side 302 of the device 300 faces outwardly from a diaper in use and includes a decorative design. The bottom side 304 of the device includes a window 306 through which a light source, such as the LED light source 204 shown in FIG. 6, may transmit to an indicator disposed within the diaper and a color sensor may detect one or more colors of the indicator. In the particular embodiment shown in FIG. 7, for example, the a plurality of screws 308 or other connectors may secure the top and bottom components to each other. The side 310 includes a notch 312 or other opening to assist a user to separate the top and bottom sides 302, 304 if the screws 308 are disengaged.

The container of the detector device 300 maybe sized and shaped to prevent the device 300 from being a choking hazard. The container may further include materials such as silicone, Tecaform, Tecanat or other materials. The device container may also include one or more muted colors to minimize its attractiveness to children.

FIG. 8 shows an example embodiment an attachment zone 400 of a diaper exterior adapted for receiving a detector device, such as the detector device shown in FIGS. 6 and 7. The attachment zone 400 includes a landing zone material 402 to improve attachment of the detector device to the diaper. The landing zone material 402, for example, may include a brushknit or adhesive or cohesive tape material for mechanically or adhesively coupling the detector device to an outer surface of the diaper. The landing zone material 402 includes a window opening 404 that corresponds to the window of the detector device (e.g., window 306 shown in FIG. 7). In one particular implementation, the landing zone material 402 may be sized and shaped similarly to the detector device so as to facilitate placement of the detector device on the outer surface of the diaper. Other landing zone materials are also contemplated. For example, loop, hook, adhesive, strap, button, snap, pocket, magnet, or other materials may be used on the diaper and/or detector device.

Figure 9:
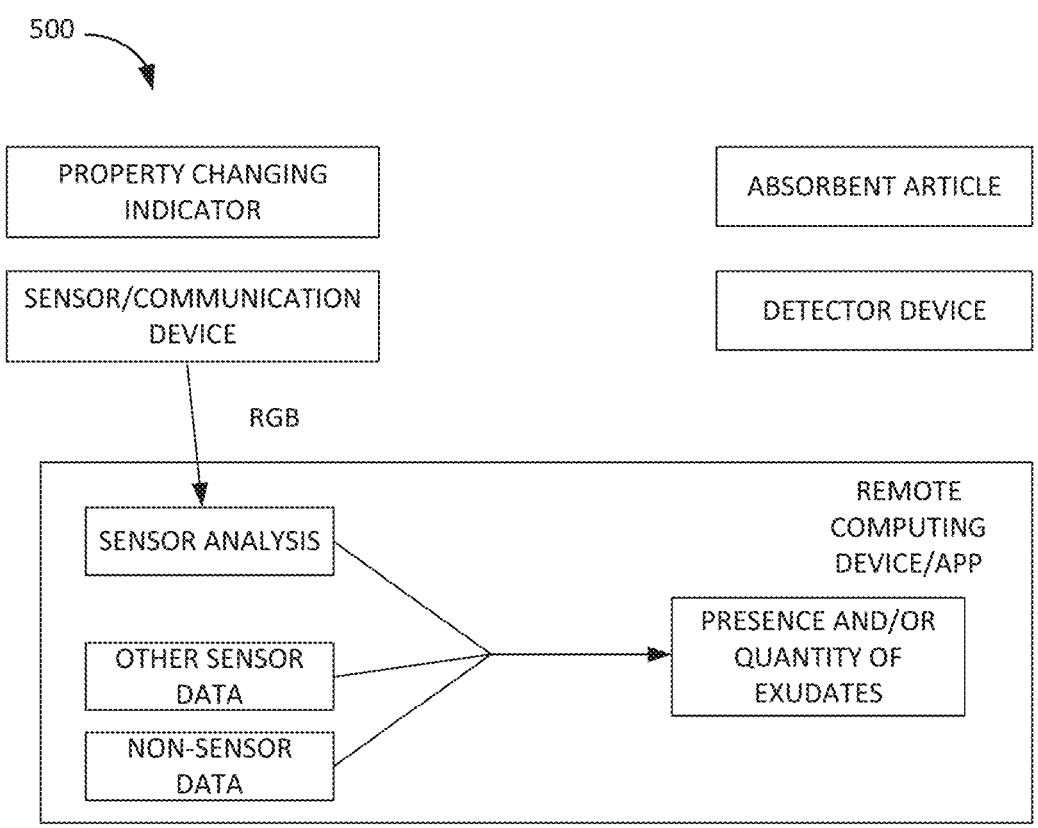
FIG. 9 shows a flow diagram of example operations that may be used to detect one or more bodily exudates within a diaper

FIG. 9 shows a flow diagram of example operations that may be used to detect one or more bodily exudates within a diaper. In this embodiment, a detector device includes one or more color sensors for detecting one or more state of an indicator in a diaper. As described above, a color sensor of the detector device may determine one or more RGB light levels or HSB levels of the indicator. A communications device of the detector device may provide information based upon a detected color of the indicator to a remote computing device. The remote computing device then predicts presence, absence and/or amount of one or more bodily exudates based at least in part on the information received from the detector device. The remote computing device, for example, may determine a local saturation (e.g., exudate content quantity) level based upon the information received from the detector device.

The remote computing device may further receive additional inputs, such as but not limited to, weartime, the time the absorbent article was attached to a wearer, the current time, absorbent article user information (e.g., baby demographic information such as sex, age, weight of wearer, whether the wearer is toilet training, degree of wearer incontinence), user input information, caregiver preference information, biometric information of the wearer, ambient sensor information and/or contextual information, and may use these additional inputs separately and/or in combination with the information received from the detector device.

In the particular embodiment, shown in FIG. 9, for example, the remote computing device determines a predicted diaper fullness level (e.g., an exudate content quantity of the absorbent article such as a liquid and/or solid exudate content quantity) or state based at least in part upon the sensor information received from the detector device and contextual information (e.g., wear time of the diaper and baby demographic information). Contextual information, for example, may be input by consumers, retrieved via other sensors or information sources (e.g., thermostats). Sensor data, for example, may include property change indications (e.g., digital or analog such as an intensity of color change in a color changing indicator) and wear time. In one implementation, an analog detection may be based upon a calibration of an indicator (e.g., color) for different exudate loads. Wear time, for example, may be described as the time determined between attachments of two fresh diapers.

Further, in one example, exudate fullness may be determined by the following functions:

Urine Fullness=$f$(Property Change Detection, wear time, wearer data and other data)

Property Change Detection=$f$(color sensor data).

An exudate content quantity, for example, may be provided to a user to indicate a percent or other indication of diaper fullness or remaining capacity on the detector device, a remote display or a remote computing device. In one particular implementation, for example, the remote display or computing device may display a graphical or numerical representation of exudate content quantity or remaining capacity of the absorbent article.

Calibration of the color of the indicator to a particular exudate load quantity, for example, can be determined in a number of manners. For example, in one embodiment, different load quantities of an absorbent article may be introduced and corresponding colors can then be measured. In another embodiment, for a given load quantity, a color change may be mapped versus time measured during loading to provide a kinetic curve that represents an exudate load quantity versus time.

Figure 10:
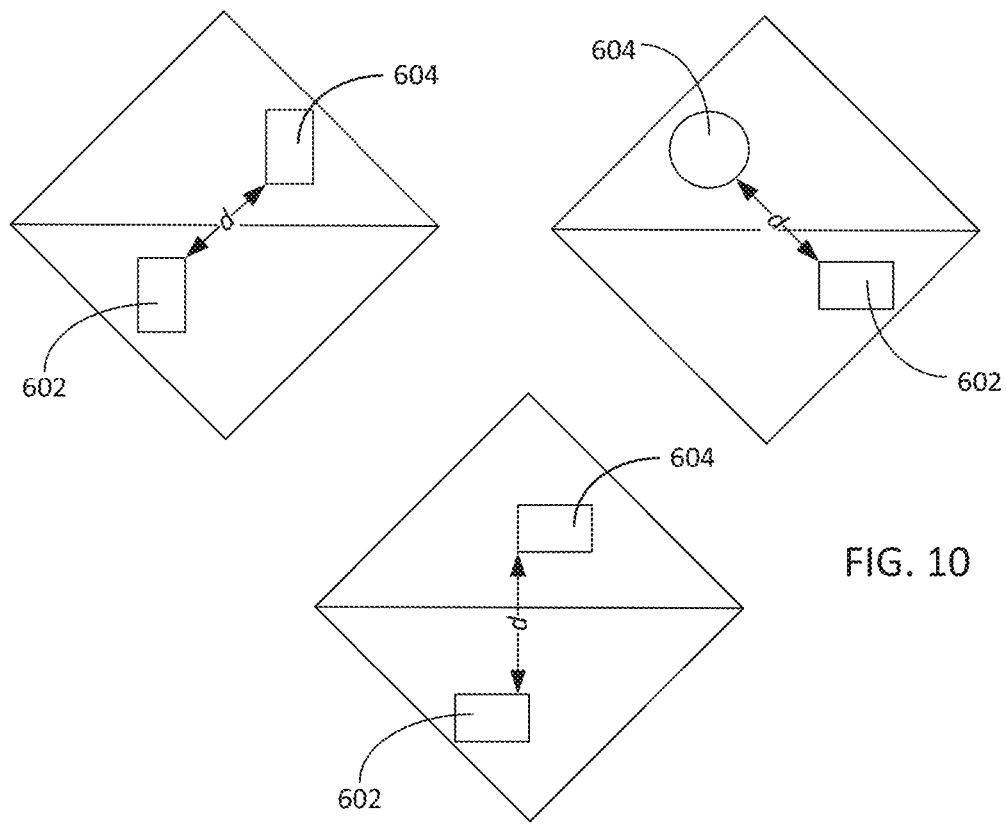
FIG. 10 shows example embodiments of spaced optical sensor and light element 604 pairs of example embodiments of one or more detector devices.

FIG. 10 shows example embodiments of spaced optical sensor 602 and light element 604 pairs of example embodiments of one or more detector devices. In these embodiment, various combinations of sensors (e.g., optical and/or color sensors) are spaced by a distance d from each other. For purposes of the present disclosure, the measurement d is a straight line measurement from the nearest points of the various optical sensors 602 and light elements 604. In one example embodiment, for example, the optical sensor 602 and light element 604 are spaced at least about 5 mm from each other. In other embodiments, the optical sensor 602 and light element 604 are spaced at least about 8 mm, at least about 10 mm, between about 10 mm and about 15 mm and between about 10 mm and 20 mm.

Figure 11:
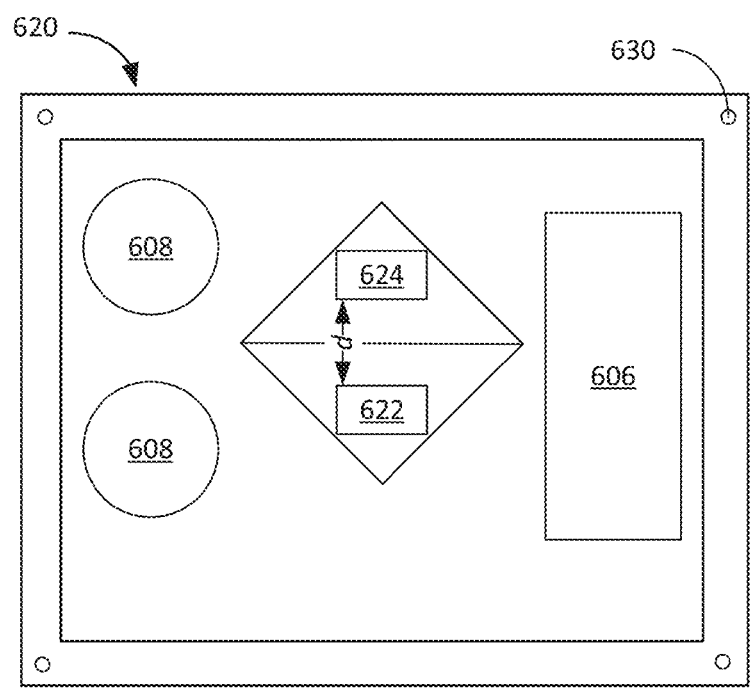
FIG. 11 shows another example embodiment of a detector device. In this embodiment, for example, an optical sensor and a light element are spaced from each other.

FIG. 11 shows another example embodiment of a detector device 620. In this embodiment, for example, an optical sensor 622 and a light element 624 are spaced from each other a distance d. The detector device 620 further includes a communication module 606 and a pair of batteries 608. Screw holes 630 are also provided to allow a cover to be securely fastened to enclose the components of the detector device. As described above, the detector device 620 may further include a window opposing the spaced optical sensor 622 and light element 624.

Figure 12:
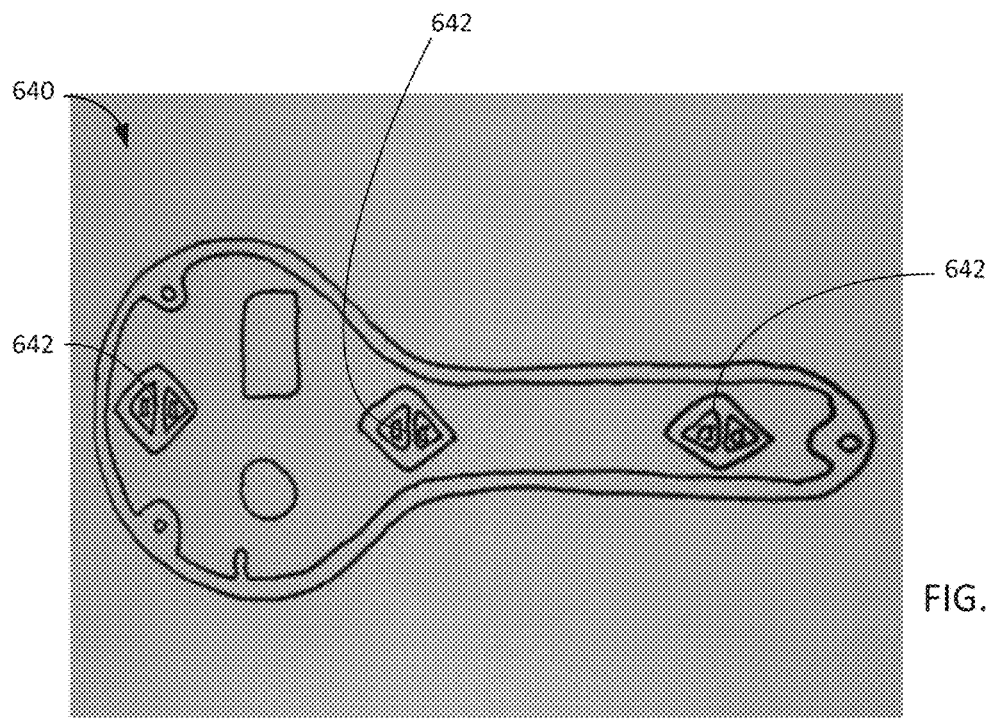
FIG. 12 shows another example embodiment of a detector device comprising a plurality of spaced optical sensor and light pairs.

FIG. 12 shows another example embodiment of a detector device 640 comprising a plurality of spaced optical sensor and light pairs 642. In this particular embodiment, three pairs of individual spaced optical sensor and light pairs 642 are disposed in different locations of the detector device 640 and adapted to detect a change in one or more optical properties at different locations of an absorbent article. The detector device 640 further comprises a communication module 646 and a battery 648 adapted to provide power to the sensors, lights and communication module 646.

Figure 13:
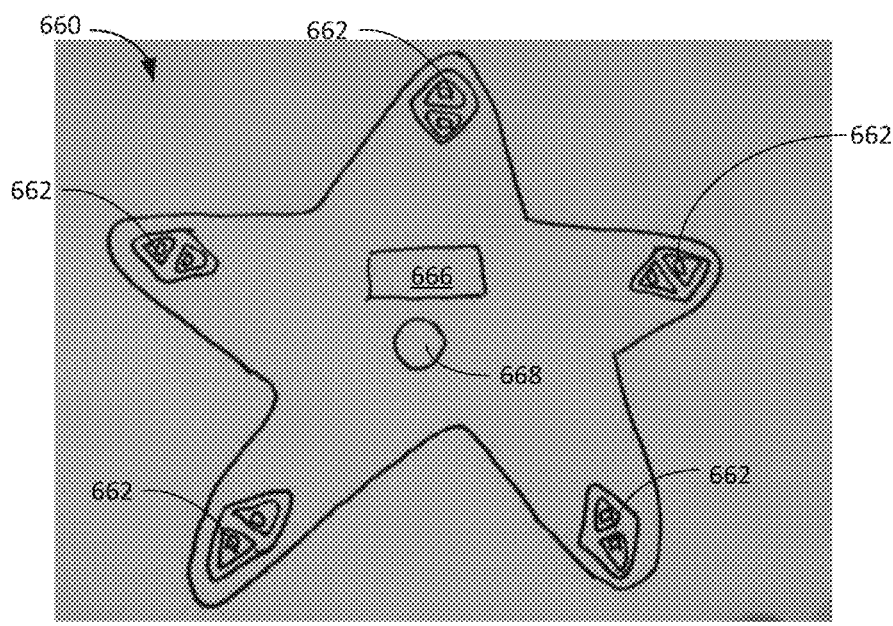
FIG. 13 shows yet another example embodiment of a detector device comprising a plurality of spaced optical sensor and light pairs.

FIG. 13 shows yet another example embodiment of a detector device 660 comprising a plurality of spaced optical sensor and light pairs 662. In this particular embodiment, five pairs of individual spaced optical sensor and light pairs 662 are disposed in different locations of the detector device 660 and adapted to detect a change in one or more optical properties at different locations of an absorbent article. The detector device 660 further comprises a communication module 646 and a battery 668 adapted to provide power to the sensors, lights and communication module 646.

Figure 14:
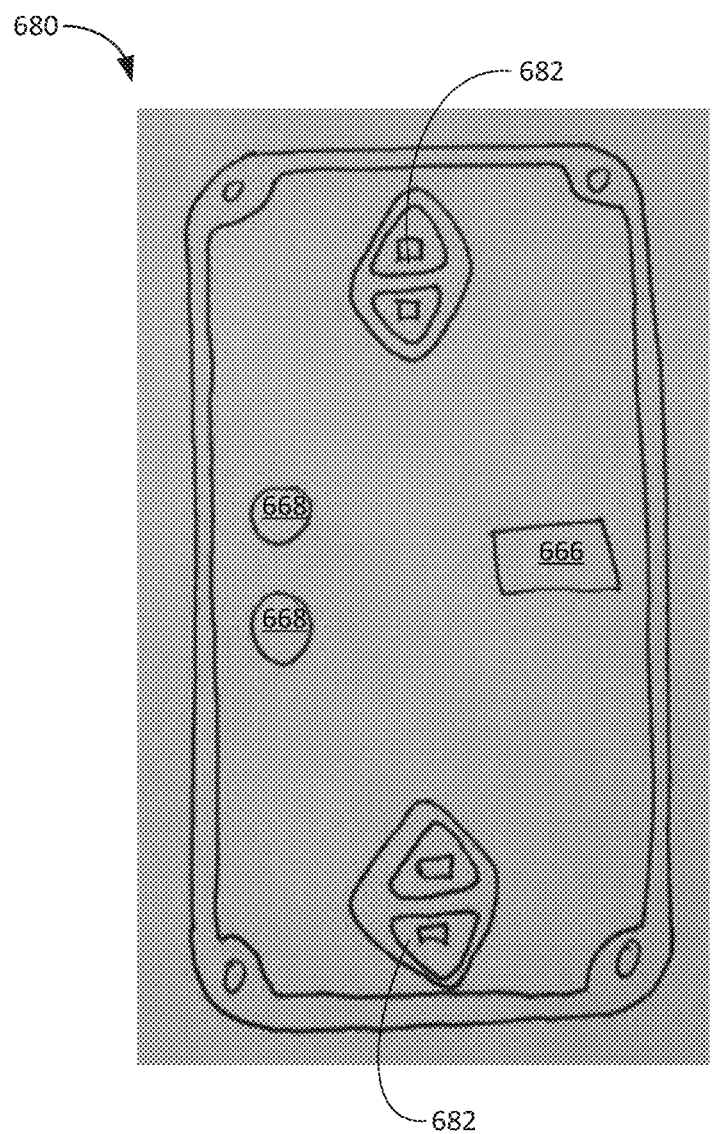
FIG. 14 shows still another example embodiment of a detector devise comprising a plurality of spaced optical sensor and light pairs.

FIG. 14 shows still another example embodiment of a detector device 680 comprising a plurality of spaced optical sensor and light pairs 682. In this particular embodiment, two pairs of individual spaced optical sensor and light pairs 682 are disposed in different locations of the detector device 680 and adapted to detect a change in one or more optical properties at different locations of an absorbent article. The detector device 680 further comprises a communication module 686 and a battery 688 adapted to provide power to the sensors, lights and communication module 686.

Figure 15:
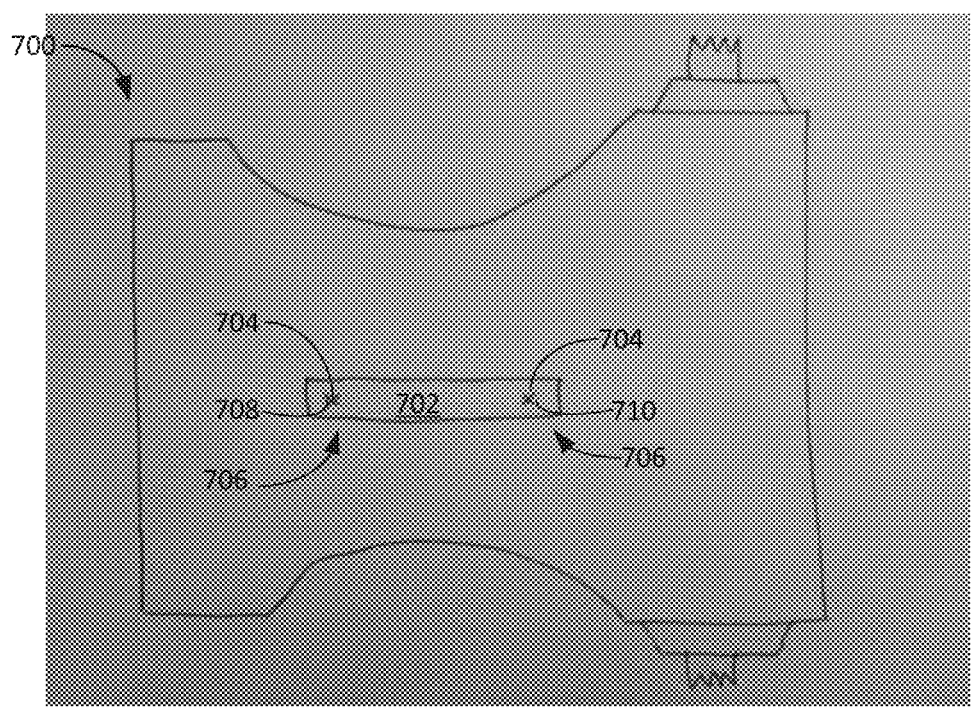
FIG. 15 shows an example embodiment of an absorbent article including a detector device coupled to the absorbent article.

FIG. 15 shows an example embodiment of an absorbent article 700 including a detector device 702 disposed adjacent to the absorbent article 700. In this particular embodiment, the detector device comprises a plurality of sensors 704. Each of the plurality of sensors 704 is spaced from each other and adapted to be disposed opposite different locations 706 of the absorbent article 700. As shown in FIG. 15, for example, a first sensor 708 is disposed opposite a front region of the absorbent article 700 and a second sensor 710 is disposed opposite a crotch region of the absorbent article 700. The first and second sensors 708, 710, for example, may be spaced at least about 2 cm from each other, at least about 3 cm from each other, at least about 4 cm from each other, at least about 5 cm from each other, or at least about 10 cm from each other. This allows the sensors to detect property changes (e.g., optical/color property changes) in different regions of the absorbent article 700. Further, the plurality of sensors 704 may comprise the same or different types of sensors.

By measuring changes in multiple areas of the absorbent article, the detector device may be able to provide a better prediction of the presence and/or quantity of bodily exudates within the absorbent article given the broad distribution of urination patterns, urination loads, dietary habits, wearer movement and activity during wear time, wearer body dimensions and the like, all of which may have an effect on exudate distribution within the absorbent article.

Figures 16, 17:
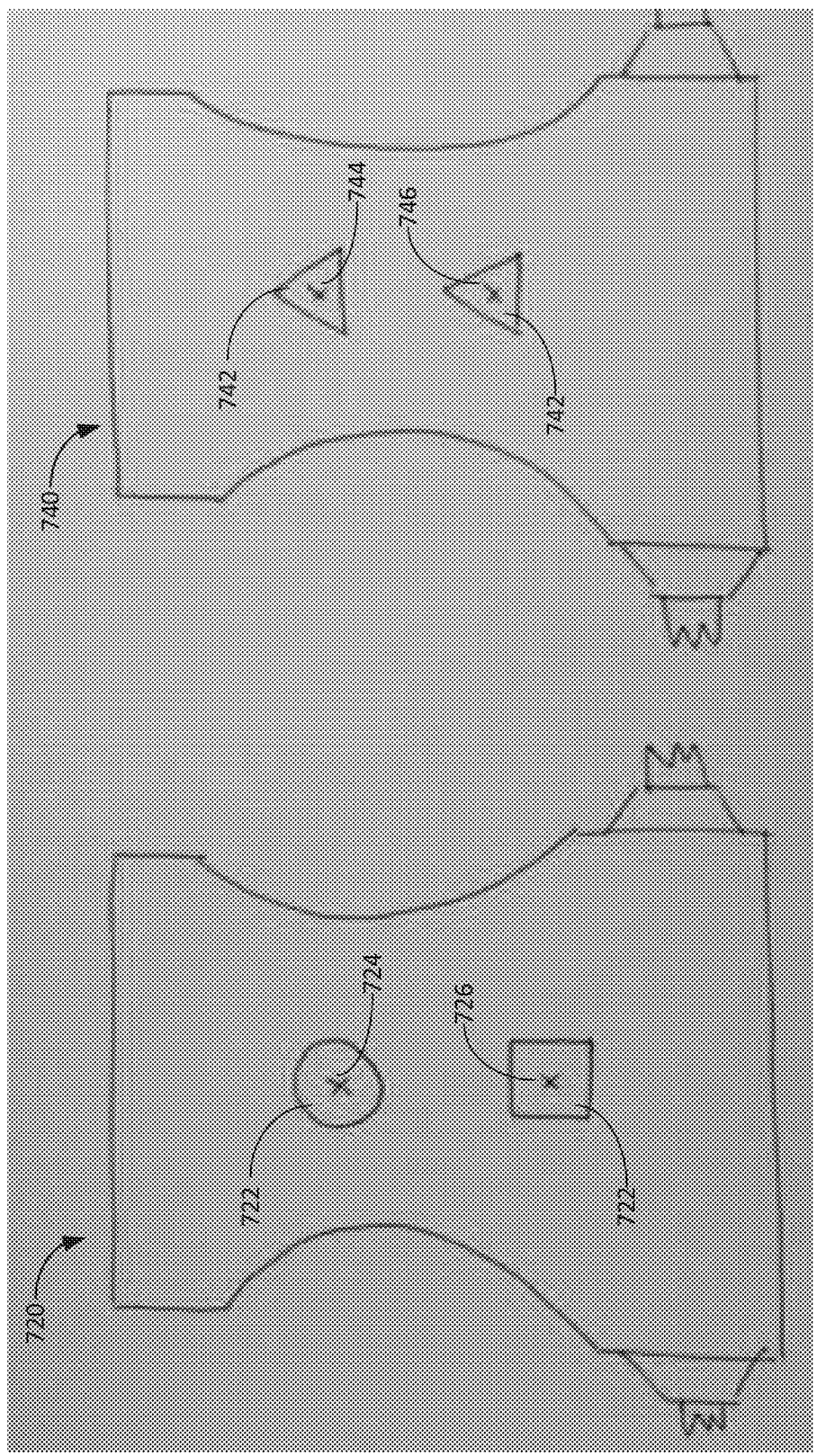
FIG. 16 shows another example embodiment of an absorbent article including a plurality of property changing indicators disposed within the absorbent article.
FIG. 17 shows yet another example embodiment of an absorbent article including a plurality of property changing indicators disposed within the absorbent article.

FIG. 16 shows another example embodiment of an absorbent article 720 including a plurality of property changing indicators 722 disposed within the absorbent article 720. In this embodiment, for example, the plurality of property changing indicators 722 comprises at least a first property changing indicator 724 of a first type and a second property changing indicator 726 of a second type that is different from the first type.

FIG. 17 shows yet another example embodiment of an absorbent article 740 including a plurality of property changing indicators 742 disposed within the absorbent article 740. In this embodiment, for example, the plurality of property changing indicators 742 comprises at least a first property changing indicator 724 and a second property changing indicator 726 of the same type of property changing indicator.

In addition to the sensors described herein adapted to detect one or more property changes of an indicator, the detector devices may further include one or more additional sensors adapted to detect other conditions unrelated to the specific indicators of an absorbent article. For example, the detector device may further include one or more additional sensors such as, but not limited to, a temperature sensor, a humidity sensor, a relative humidity sensor, an electrical sensor, a resistance sensor, a capacitive sensor, an inductive sensor, a continuity sensor, a chemical sensor, an audio sensor, a microphone, a strain gauge, a material expansion sensor and a vibration sensor.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

What is claimed is:

1. A system for monitoring an absorbent article designed to absorb and contain bodily exudates, the system comprising:

an absorbent article comprising an optical property changing indicator adapted to change at least one optical property in response to the presence or absence of bodily exudates, wherein the absorbent article and the indicator form one integral unit; and an optical sensor detector device comprising a housing, a battery disposed within the housing, an optical sensor disposed within the housing, a processor and memory storage disposed within the housing to provide data processing on the optical sensor detector device, and a powered light source disposed within the housing and spaced from the optical sensor, the optical sensor adapted to detect the change of the optical property of the indicator, wherein at least one of the absorbent article and the detector device is adapted to be associated together and disassociated from each other, wherein when the absorbent article and the detector device are associated together the light source emits light in a direction towards the absorbent article and the detector device is adapted to detect the change of optical property of the indicator.

2. The system of claim 1 wherein the optical sensor comprises a color sensor detector device.

3. The system of claim 1 wherein the light source comprises at least one of the group comprising: an LED and an OLED.

4. The system of claim 3 wherein the optical sensor comprises at least one of the group comprising: a photodiode, phototransistor, electron tube detector, photosensor, photomultiplier tube, phototube, photodetector, opto-semiconductor detector, photodiode, phototransistor, photomultiplier, image sensor, infrared detector, thermal sensor, illuminance sensor, visible light sensor and color sensor.

5. The system of claim 1 wherein the light source and sensor of the optical sensor detector device are spaced at least about 5 mm apart from each other.

6. The system of claim 1 wherein the optical property changing indicator comprises a chemical substance which induces a color change when at least one bodily exudate is present.

7. The system of claim 1 wherein the absorbent article comprises a connector selected from at least one of the group comprising: a pocket, a sleeve, a loop, an adhesive, an adhesive tape, a mechanical fastener, a hook fastener, a loop fastener, a snap, a slot, a hole, a button, a belt, a magnet, a magnetic fastener, a paramagnetic fastener, a cohesive fastener and a strap.

8. The system of claim 7 wherein the absorbent article connector is adapted to attach the detector device to the absorbent article juxtaposed the property changing indicator of the absorbent article.

9. The system of claim 1 wherein the detector device comprises at least one of the group comprising: a loop, an adhesive, an adhesive tape, a mechanical fastener, a hook fastener, a loop fastener, a snap, a slot, a hole, a button, a belt, a magnet, a magnetic fastener, a paramagnetic fastener, a cohesive fastener and a strap.

10. The system of claim 1 wherein the detector device can provide information to a display element.

11. The system of claim 10 wherein the display element is provided in a separate unit.

12. The system of claim 1 wherein the absorbent article comprises a topsheet facing the wearer, a backsheet, generally co-extensive with the topsheet and facing away from the wearer and an absorbent core, encased between the topsheet and the backsheet and wherein the optical property changing indicator is disposed between the backsheet and the core.

13. The system of claim 1 wherein an exudate content quantity of the absorbent article is determined based at least in part upon the optical property change detected via the optical sensor.

14. The system of claim 1 wherein the optical sensor is adapted to detect graduated optical property changes of the absorbent article.

15. The system of claim 1 wherein an exudate content quantity of the absorbent article is determined based at least in part upon detected graduated optical property changes of the absorbent article.

16. The system of claim 1 wherein the detector device comprises a communication module selected from at least one of the group comprising: a Bluetooth communication module, a BTLE communication module, a mesh communication module, a WiFi communication module, a communication module incorporating one or more protocols defined in IEEE 802, an RFID module, a 3G communication module, a 4G communication module, a Backscatter communication module, a light communication module, a sound communication module, and a harvesting protocol communication module.

* * * * *